(12) United States Patent
Sabelle et al.

(10) Patent No.: US 6,946,005 B2
(45) Date of Patent: Sep. 20, 2005

(54) PYRROLIDINYL-SUBSTITUTED PARA-PHENYLENEDIAMINE DERIVATIVES SUBSTITUTED WITH A CATIONIC RADICAL, AND USE OF THESE DERIVATIVES FOR DYEING KERATIN FIBERS

(75) Inventors: Stéphane Sabelle, Paris (FR); Laure Ramos, Bourg Lareine (FR); Madeleine Leduc, Paris (FR); Michel Philippe, Wissous (FR)

(73) Assignee: L'Oreal S.A., Paris (FR)

( * ) Notice: Subject to any disclaimer, the term of this patent is extended or adjusted under 35 U.S.C. 154(b) by 122 days.

(21) Appl. No.: 10/397,245

(22) Filed: Mar. 27, 2003

(65) Prior Publication Data

US 2003/0229949 A1 Dec. 18, 2003
US 2004/0194227 A9 Dec. 18, 2003

Related U.S. Application Data

(60) Provisional application No. 60/387,499, filed on Jun. 11, 2002.

(30) Foreign Application Priority Data

Mar. 27, 2002 (FR) .......................................... 02 03847

(51) Int. Cl.$^7$ ................................................. A61K 7/13
(52) U.S. Cl. ...................... 8/405; 8/406; 8/409; 8/410; 8/540; 8/574; 548/557
(58) Field of Search ......................... 8/405, 406, 409, 8/410, 540, 574; 548/557

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 280/583 |
| 2,388,614 A | 11/1945 | Kirby et al. | 167/22 |
| 2,454,547 A | 11/1948 | Bock et al. | 260/567.8 |
| 3,061,432 A | 10/1962 | Menzel et al. | 96/35 |
| 3,206,462 A | 9/1965 | McCarty | 260/256.4 |
| 3,227,554 A | 1/1966 | Barr et al. | 96/55 |
| 3,419,391 A | 12/1968 | Young | 96/56.5 |
| 3,725,067 A | 4/1973 | Bailey et al. | 96/56.5 |
| 3,758,309 A | 9/1973 | Bailey et al. | 96/136 |
| 3,874,870 A | 4/1975 | Green et al. | 71/67 |
| 3,915,921 A | 10/1975 | Schlatzer, Jr. | 260/17.4 |
| 3,926,631 A | 12/1975 | Arai et al. | 96/29 D |
| 3,929,990 A | 12/1975 | Green et al. | 424/78 |
| 3,966,904 A | 6/1976 | Green et al. | 424/78 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567 |
| 4,027,020 A | 5/1977 | Green et al. | 424/248 |
| 4,128,425 A | 12/1978 | Greenwald | 96/66 |
| 4,157,388 A | 6/1979 | Christiansen | 424/70 |
| 4,349,532 A | 9/1982 | Vanlerberghe et al. | 424/47 |
| 4,390,689 A | 6/1983 | Jacquet et al. | 528/335 |
| 4,500,548 A | 2/1985 | Silva | 426/19 |
| 4,500,630 A | 2/1985 | Sato et al. | 430/386 |
| 4,509,949 A | 4/1985 | Huang et al. | 586/558 |
| 4,540,654 A | 9/1985 | Sato et al. | 430/381 |
| 4,608,250 A | 8/1986 | Jacquet et al. | 424/71 |
| 4,621,046 A | 11/1986 | Sato et al. | 430/381 |
| 4,702,906 A | 10/1987 | Jacquet et al. | 424/70 |
| 4,719,282 A | 1/1988 | Nadolsky et al. | 528/310 |
| 4,823,985 A | 4/1989 | Grollier et al. | 222/1 |
| 4,842,849 A | 6/1989 | Grollier et al. | 424/70 |
| 5,061,289 A | 10/1991 | Clausen et al. | 8/405 |
| 5,135,543 A | 8/1992 | Chan et al. | 8/405 |
| 5,196,189 A | 3/1993 | Jacquet et al. | 424/72 |
| 5,256,526 A | 10/1993 | Suzuki et al. | 430/384 |
| 5,278,034 A | 1/1994 | Ohki et al. | 430/440 |
| 5,380,340 A | 1/1995 | Neunhoeffer et al. | 8/409 |
| 5,441,863 A | 8/1995 | Tang et al. | 430/558 |
| 5,457,210 A | 10/1995 | Kim et al. | 548/262.4 |
| 5,538,516 A | 7/1996 | Audousset et al. | 8/412 |
| 5,707,786 A | 1/1998 | Schmuck et al. | 430/373 |
| 5,708,151 A | 1/1998 | Mockli | 534/608 |
| 5,735,908 A | 4/1998 | Cotteret et al. | 8/410 |
| 5,766,576 A | 6/1998 | Löwe et al. | 424/62 |
| 5,769,903 A | 6/1998 | Audousset et al. | 8/409 |
| 5,785,717 A | 7/1998 | Maubru et al. | 8/409 |
| 5,851,237 A | 12/1998 | Anderson et al. | 8/409 |
| 5,876,464 A | 3/1999 | Lim et al. | 8/409 |
| 5,993,491 A | 11/1999 | Lim et al. | 8/409 |
| 6,042,620 A | 3/2000 | Braun et al. | 8/410 |
| 6,099,592 A | 8/2000 | Vidal et al. | 8/409 |

(Continued)

FOREIGN PATENT DOCUMENTS

| | | |
|---|---|---|
| DE | 23 59 399 | 1/1975 |
| DE | 38 43 892 | 6/1990 |
| DE | 41 33 957 | 4/1993 |

(Continued)

OTHER PUBLICATIONS

English language Derwent Abstract of EP 0 770 375, May 2, 1997.
English language Derwent Abstract of FR 2 766 178, Jan. 22, 1999.
English language Derwent Abstract of FR 2 801 308, May 25, 2001.

(Continued)

Primary Examiner—Margaret Einsmann
Assistant Examiner—Eisa Elhilo
(74) Attorney, Agent, or Firm—Finnegan, Henderson, Farabow, Garrett & Dunner, L.L.P.

(57) ABSTRACT

Novel pyrrolidinyl-substituted para-phenylenediamine derivatives comprising a cationic radical, the dye compositions comprising them and the process for dyeing keratin fibers using these compositions, making it possible to obtain a chromatic, powerful, unselective and fast coloration of keratin fibers.

36 Claims, No Drawings

U.S. PATENT DOCUMENTS

| | | | |
|---|---|---|---|
| 6,099,593 A | 8/2000 | Terranova et al. | 8/409 |
| 6,165,230 A | 12/2000 | Rose et al. | 8/409 |
| 6,461,391 B1 * | 10/2002 | Lim et al. | 8/405 |
| 8,464,731 | 10/2002 | Genet et al. | 8/405 |
| 6,521,761 B2 | 2/2003 | Lim et al. | 548/557 |
| 6,613,313 B2 | 9/2003 | Kimura | 424/70.1 |
| 6,638,321 B1 | 10/2003 | Genet et al. | 8/407 |
| 2002/0197223 A1 | 12/2002 | Kimura | 424/70.1 |
| 2003/0093866 A1 | 5/2003 | Vidal et al. | 8/405 |
| 2003/0150066 A1 | 8/2003 | Richard | 8/405 |
| 2004/0064902 A1 | 4/2004 | Sabelle et al. | 8/405 |
| 2004/0074013 A1 | 4/2004 | Terranova et al. | 8/405 |
| 2004/0078905 A1 | 4/2004 | Terranova et al. | 8/405 |
| 2004/0083559 A1 | 5/2004 | Sabelle et al. | 8/405 |
| 2004/0088799 A1 | 5/2004 | Sabelle et al. | 8/405 |

FOREIGN PATENT DOCUMENTS

| | | |
|---|---|---|
| DE | 42 34 886 A1 | 4/1994 |
| DE | 42 41 532 | 6/1994 |
| DE | 299 01 593 | 4/1999 |
| DE | 195 43 988 | 5/1999 |
| DE | 299 02 262 | 5/1999 |
| DE | 100 34 617 A1 | 1/2002 |
| EP | 0 119 860 | 9/1984 |
| EP | 0 122 324 | 10/1984 |
| EP | 0 173 109 | 3/1986 |
| EP | 0 216 479 | 4/1987 |
| EP | 0 244 160 | 11/1987 |
| EP | 0 285 274 | 10/1988 |
| EP | 0 304 001 | 2/1989 |
| EP | 0 456 226 | 11/1991 |
| EP | 0 488 248 | 6/1992 |
| EP | 0 488 909 | 6/1992 |
| EP | 0 518 238 | 12/1992 |
| EP | 0 557 851 | 9/1993 |
| EP | 0 578 248 | 1/1994 |
| EP | 0 714 954 | 6/1996 |
| EP | 0 770 375 | 5/1997 |
| EP | 0 943 614 A2 | 9/1999 |
| EP | 0 962 452 | 12/1999 |
| EP | 1 018 508 | 7/2000 |
| FR | 1 400 366 | 4/1965 |
| FR | 2 075 583 | 10/1971 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 413 907 | 8/1979 |
| FR | 2 586 913 | 3/1987 |
| FR | 2 733 749 | 11/1996 |
| FR | 2 750 048 | 12/1997 |
| FR | 2 766 178 | 1/1999 |
| FR | 2 801 308 | 5/2001 |
| GB | 1 021 400 | 3/1966 |
| GB | 1 026 978 | 4/1966 |
| GB | 1 153 196 | 5/1969 |
| GB | 1 458 377 | 12/1976 |
| GB | 169571 | 7/1988 |
| GB | 2 239 265 | 6/1991 |
| JP | 58-42045 | 3/1983 |
| JP | 59-98437 | 6/1984 |
| JP | 59-99437 | 6/1984 |
| JP | 59-162548 | 9/1984 |
| JP | 59-171956 | 9/1984 |
| JP | 60-33552 | 2/1985 |
| JP | 60-43659 | 3/1985 |
| JP | 60-172982 | 9/1985 |
| JP | 60-190779 | 9/1985 |
| JP | 62-279337 | 12/1987 |
| JP | 1-115048 | 5/1989 |
| JP | 2-19576 | 1/1990 |
| JP | 5-163124 | 6/1993 |
| JP | 6-236011 | 8/1994 |
| JP | 7-36159 | 2/1995 |
| JP | 7-84348 | 3/1995 |
| JP | 7-92632 | 4/1995 |
| JP | 7-98489 | 4/1995 |
| JP | 7-244361 | 9/1995 |
| JP | 7-325375 | 12/1995 |
| JP | 11-158048 | 6/1999 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 98/01106 | 1/1998 |
| WO | WO 98/38175 | 9/1998 |
| WO | WO 99/03819 | 1/1999 |
| WO | WO099/17725 | 4/1999 |
| WO | WO 99/64417 | 12/1999 |
| WO | WO 01/68043 | 9/2001 |
| WO | WO 02/45675 | 6/2002 |

OTHER PUBLICATIONS

English language Derwent Abstract of JP 2–19576, Jan. 23, 1990.

English language Derwent Abstract of JP 11–158048, Jun. 15, 1999.

Co–pending U.S. Appl. No. 09/959,913, filed Mar. 31, 2001.

Co–pending U.S. Appl. No. 10/433,408, filed Jun. 4, 2003.

Co–pending U.S. Appl. No. 10/433,411, filed Oct. 29, 2003.

Co–pending U.S. Appl. No. 10/433,687, filed Jun. 5, 2003.

Co–pending U.S. Appl. No. 10/433,688, filed Nov. 5, 2003.

Co–pending U.S. Appl. No. 10/433,689, filed Nov. 12, 2003.

Co–pending U.S. Appl. No. 10/603,831, filed Jun. 26, 2003.

Co–pending U.S. Appl. No. 10/612,986, filed Jul. 7, 2003.

Co–pending U.S. Appl. No. 10/657,245, filed Dec. 9, 2003.

E. Hannig et al., "Kurze Orginalmitteilungen", Die Pharmazie, p. 231, 1980.

E.J. Browne et al., "Triazoles, Part VII.* Syntheses of Substituted 1,2,4–Triazoles", Journal of The Chemical Society, pp. 5149–5152, 1962.

English language Derwent Abstract of De 100 34 617, Jan. 31, 2002.

English language Derwent Abstract of DE 195 43 988, May 28, 1997.

English language Derwent Abstract of DE 23 59 399, Jun. 12, 1975.

English language Derwent Abstract of DE 299 01 593, Apr. 8, 1999.

English language Derwent Abstract of DE 299 02 262, May 6, 1999.

English language Derwent Abstract of DE 38 43 892, Jun. 28, 1990.

English language Derwent Abstract of DE 41 33 957, Apr. 15, 1993.

English language Derwent Abstract of DE 42 34 886, Apr. 21, 1994.

English language Derwent Abstract of DE 42 41 532, Jun. 16, 1994.

English language Derwent Abstract of EP 0 943 614, Dec. 12, 2001.

English language Derwent Abstract of FR 2 320 330, Mar. 4, 1977.

English language Derwent Abstract of FR 2 336 434, Jul. 22, 1977.
English language Derwent Abstract of FR 2 586 913, Mar. 13, 1987.
English language Derwent Abstract of FR 2 733 749, Nov. 8, 1996.
English language Derwent Abstract of FR 2 750 048, Dec. 26, 1997.
English language Derwent Abstract of JP 1–115048, May 8, 1989.
English language Derwent Abstract of JP 5–163124, Jun. 19, 1993.
English language Derwent Abstract of JP 58042045, Mar. 11, 1983.
English language Derwent Abstract of JP 5999437, Jun. 8, 1984.
English language Derwent Abstract of JP 60190779, Sep. 28, 1985.
English language Derwent Abstract of JP 6033552, Feb. 20, 1985.
English language Derwent Abstract of JP 6043659, Mar. 8, 1985.
English language Derwent Abstract of JP 62279337, Dec. 4, 1987.
English language Derwent Abstract of JP 6236011, Aug. 23, 1994.
English language Derwent Abstract of JP 7036159, Feb. 7, 1995.
English language Derwent Abstract of JP 7084348, Mar. 31, 1995.
English language Derwent Abstract of JP 7092632, Apr. 7, 1995.
English language Derwent Abstract of JP 7098489, Apr. 11, 1995.
English language Derwent Abstract of JP 7244361, Sep. 19, 1995.
English language Derwent Abstract of JP 7325375, Dec. 12, 1995.
English language Derwent Abstract of JP application 88–169571.
Eser Ilhan, et al., "Synthese von 6–Benzyliden–2–(a,a–diphenyl–a–hydroxyacetyl)–thiazolo[3,2–b]–s–frialzol–5–onen als potentiell biologisch wirksame Stroffe", Archiv der Pharmazie, pp. 825–826, 1994.
French Search Report of FR 02/03847, Nov. 25, 2002.
French Search Report for FR 02/07939, Feb. 17, 2003.
French Search Report for FR 02/08514, Mar. 20, 2003.
French Search Report for FR 02/11133, May 15, 2003.
G. Fonnum et al., "Associative thickeners. Part I: Synthesis, rheology and aggregation behavior", Colloid & Polymer Science, 271, pp. 380–389, 1993.
Giuliana Cardillo et al., "Sulle 1,2–difenil–3,5–dichetopirazolidine", Gazzetta Chimica Italiana, vol. 96, pp. 973–985, 1966.
H. Koopman, :"Investigations on Herbicides IV, The synthesis of 2,6–dichlorobenzonitrile", Recueil, pp. 1075–1083, 1961.
Hans Beyer et al., "Uber die Pyrazolbidung aus alpha–Chlor–acetessigester und Thiocarbohydrazid," Chemische Berichte, pp 2550–2555, 1956.
Henryk Foks et al., "Synthesis and Biological Activity of Thiazolo–1,2,4–Triazoles", Acta Poloniae Pharmaceutica—Drug Research, pp. 415–420, 1995.

International Search Report for PCT/FR 01/00745, Sep. 14, 2001.
International Search Report for PCT/FR 01/03540, Mar. 11, 2002.
International Search Report for PCT/FR 01/03541, Mar. 11, 2002.
International Search Report for PCT/FR 01/03542, Mar. 11, 2002.
International Search Report for PCT/FR 01/03543, Mar. 14, 2002.
International Search Report for PCT/FR 01/03571, Mar. 11, 2002.
Joseph Bailey, "Synthesis of 1 H–Pyrazolo[3,2–c]–s–Triazoles and Derived Azamethine Dyes," Journal of The Chemical Society, pp 2047–2052, 1977.
Lidia Wyzgowska, et al., "O Reakcjach Trikarboetoksymetanu", Acta Poloniae Pharmaceutica, pp, 83–88, 1982.
Mohamed Ali et al., "Reactions with Thiazolo [3,2–b]–s–triazol–3(2H)–ones", Journal Für Praktische Chemie, pp. 12–18, 1976.
Mohamed Elnagdi et al., "Routes for the Synthesis of 3,5–Diaminopyrazoles, 2–Aminopyrazolo[1,5–a]pyrimidines and 5–Aminopyrazolo[1,5–a]pyrimidines", Journal Für Praktische Chemie, pp .533–538, 1978.
Mohamed Elnagdi et al., "Studies on 3,5–pyrazolidinediones. IV. Addition of 4–Arylazo–3,5–pyrazolidinediones to Ethyl Acrylate", Bulletin of the Chemical Society of Japan, vol. 46, 1973. pp. 1830–1833.
Office Action in co–pending Application No. 09/656,913 dated Dec. 14, 2004 (Ex. Elhilo).
Office Action in co–pending Application No. 09/959,913 dated Dec. 16, 2003 (Ex. Elhilo).
Office Action in co–pending Application No. 10/433,411 dated Sep. 9, 2004 (Ex.Elhilo).
Office Action in co–pending Application No. 10/433,687 dated Sep. 14, 2004 (Ex. Elhilo).
Office Action in co–pending Application No. 10/433,688 dated Feb. 10, 2005 (Ex. Elhilo).
Office Action in co–pending Application No. 10/433,688 dated Sep. 9, 2004 (Ex. Elhilo).
Office Action in co–pending Application No. 10/433,689 dated Oct. 26, 2004 (Ex. Elhilo).
Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, pp. 2711–2717, 1987.
Philip Magnus et al., "Synthesis of Helical Poly–b–pyrroles. Multiple Atropisomerism Resulting in Helical Enantiomorphic Conformations", Journal of the American Chemical Society, pp. 2465–2468, 1990.
R. Stollé, "Ueber die Ueberführung der secundären Säurehydrazide in Derivate des Furodiazols, Pyrrodiazols und Thiodiazols", Berichte Der Deutschen Chemischen Gesellschaft, pp. 797–798, 1899.
R.L. Bent et al., "Chemical Constitution, Electrochemical, Photographic and Allergenic Properties of p–Amino–N–dialkylanilines," Journal of the American Chemical Society, vol. 73, No. 7, Jul. 1951, pp. 3100–3125.

S. Hiller et al., "Electron Density Distribution In Hetrocyclic Systems With Two Adjacent Nitrogen Atoms", Chemistry of Heterocyclic Compounds, pp. 93–96, 1965.

Thomas Kauffman et al., "Synthese von Amidrazonen aus Nitrilen und Natriumhydrazid", Chemische Berichte, pp 3436–3443, 1964.

Victor Cohen, "A New Method of Synthesis of Some 2–Aryl and 2–Heterocyclic Benzimidazole, Benzoxazole and Benzothiazole Derivatives", Journal of Heterocyclic Chemistry, 16, pp. 13–16, 1979.

* cited by examiner

PYRROLIDINYL-SUBSTITUTED PARA-PHENYLENEDIAMINE DERIVATIVES SUBSTITUTED WITH A CATIONIC RADICAL, AND USE OF THESE DERIVATIVES FOR DYEING KERATIN FIBERS

This application claims benefit of U.S. Provisional Application No. 60/387,499, filed Jun. 11, 2002.

The disclosure relates to novel pyrrolidinyl-substituted para-phenylenediamine derivatives comprising a cationic radical chosen from compounds of formula (I), as defined herein. This disclosure also relates to the dye compositions comprising them and the process for dyeing keratin fibers using these compositions.

It is well-known practice to dye keratin fibers, such as human hair, with dye compositions comprising oxidation dye precursors, also known as oxidation bases, such as ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives and 5,6-dihydroxyindoline derivatives. Oxidation dye precursors, or oxidation bases, are colorless or weakly colored compounds that, when combined with oxidizing products, can give rise to colored compounds and dyes by a process of oxidative condensation.

It is also known that the shades obtained with these oxidation bases may be varied by combining them with couplers or coloration modifiers. These couplers or coloration modifiers may be chosen, for example, from aromatic meta-diamines, meta-aminophenols, meta-hydroxyphenols and certain heterocyclic compounds such as, for example, pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used as oxidation bases and couplers make it possible to obtain a wide range of colors.

The "permanent" coloration obtained with these oxidation dyes should moreover satisfy a number of requirements. For example, it should have no toxicological drawbacks, it should allow shades to be obtained in the desired intensity, and it should show good resistance to external agents such as light, bad weather, washing, permanent-waving, perspiration and rubbing.

The oxidation dyes should also, for example, allow white hairs to be covered. Further, the oxidation dyes should be as unselective as possible, i.e., they should produce the smallest possible color differences along the same length of keratin fiber, which may be differently sensitized (i.e. damaged) between its end and its root. The oxidation dyes should also, for example, show good chemical stability in the formulations, and, further for example, have a good toxicological profile.

In the field of hair dyeing, para-phenylenediamine and para-tolylenediamine are oxidation bases that are widely used. These oxidation bases may, for example, provide varied shades when used with oxidation couplers.

However, there is a need to discover novel oxidation bases that may have a better toxicological profile than para-phenylenediamine and para-tolylenediamine, while at the same time may give the hair at least one of the following excellent properties: color intensity, variety of shades, color uniformity and fastness with respect to external agents.

It is already known practice to use para-phenylenediamine derivatives substituted with a pyrrolidine group as oxidation bases for dyeing keratin fibers. For example, U.S. Pat. No. 5,851,237 discloses the use of 1-(4-aminophenyl)pyrrolidine derivatives optionally substituted on the benzene nucleus, to replace para-phenylenediamine.

U.S. Pat. No. 5,993,491 discloses the use of N-(4-aminophenyl)-2-hydroxymethylpyrrolidine derivatives optionally substituted on the benzene nucleus and on the pyrrolidine heterocycle in position 4 with a hydroxyl radical, in order to replace para-phenylenediamine.

Japanese Patent Application 11-158 048 discloses compositions containing at least one compound chosen from 4-aminoaniline derivatives optionally substituted on the benzene nucleus, and one of the nitrogen atoms of which is included in a 5- to 7-membered carbon ring.

It is established that these compounds may not make it possible to give the hair a coloration that is equivalent in quality to that obtained with para-phenylenediamine or with para-tolylenediamine due to the lack of intensity and color uniformity.

There is thus a real need to discover novel oxidation bases that may, for example, have both a good toxicological profile and properties such that the compositions comprising them may be able to give the hair at least one of the following excellent properties: color intensity, variety of shades, color uniformity and fastness with respect to the various attacking factors to which the hair may be subjected.

Disclosed herein are novel dye compositions that can overcome at least one drawback of the oxidation bases of the prior art. For example, disclosed herein are novel dye compositions for dyeing keratin fibers, which do not degrade the keratin fibers, while at the same time are capable of generating intense colorations in varied shades, and which may be unselective, resistant and can have a good toxicological profile.

Further disclosed herein is a compound chosen from pyrrolidinyl-substituted para-phenylenediamine derivatives of formula (I) and the addition salts thereof

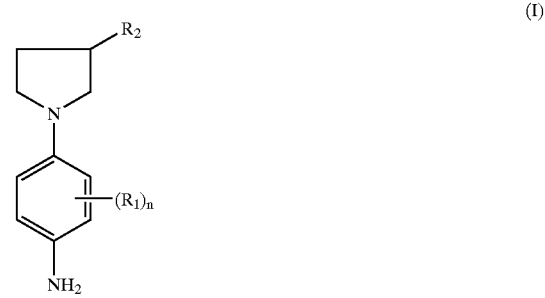

(I)

wherein
n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains wherein the hydrocarbon-based chains may be interrupted with at least one entity chosen from oxygen, nitrogen, silicon, and sulphur atoms, and a $SO_2$ radical; with the proviso that the radical $R_1$ does not comprise a peroxide bond, a diazo radical, a nitro radical or a nitroso radical, $R_2$ is chosen from onium radicals Z chosen from radicals of formulae (II), (III) and (IV), and radicals —X—C=$NR_8$—$NR_9R_{10}$, wherein X is chosen from oxygen and —NR$_{11}$ radicals, and R$_8$, R$_9$, R$_{10}$ and R$_{11}$, which may be identical or different, are each chosen from hydrogen, C$_1$–C$_4$ alkyl radicals and C$_1$–C$_4$ hydroxyalkyl radicals.

For example, R$_1$ may be chosen from a chlorine atom, and methyl, ethyl, isopropyl, vinyl, allyl, methoxymethyl, hydroxyethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy and 2-hydroxyethyloxy radicals.

Further disclosed herein is a dyeing composition comprising, in a medium suitable for dyeing keratin fibers, at least one oxidation base chosen from pyrrolidinyl-substituted para-phenylenediamine derivatives of formula (I) and the addition salts thereof.

Also disclosed herein is the use of this composition for dyeing keratin fibers and the process for dyeing keratin fibers, for example, human keratin fibers such as hair, using the composition disclosed herein.

The composition disclosed herein may make it possible to obtain, for example, a chromatic, powerful, unselective and fast coloration of keratin fibers.

As used herein, an aliphatic hydrocarbon-based chain is chosen from linear and branched chains that may comprise at least one unsaturation chosen from unsaturations of the alkene type and the alkyne type. An alicyclic hydrocarbon-based chain is chosen from saturated and unsaturated, linear and branched chains not containing an aromatic cyclic structure.

When the aliphatic hydrocarbon-based chain or the alicyclic hydrocarbon-based chain is interrupted with an entity Y chosen from an oxygen atom, a sulphur atom, a nitrogen atom, a silicon atom and a SO$_2$ radical, a unit CH$_2$—Y—CH$_2$ is obtained, for example.

The term "onium" means a nitrogen-based quaternary radical.

In formula (I), when n is equal to 1, R$_1$ may, for example, be chosen from halogen atoms; C$_1$–C$_6$ aliphatic and alicyclic, saturated and unsaturated hydrocarbon-based chains, at least one carbon atom possibly being replaced with an entity chosen from an oxygen atom, a nitrogen atom, a silicon atom, a sulphur atom, and a SO$_2$ radical, with the proviso that the radical R$_1$ does not comprise a peroxide bond, a diazo radical, a nitro radical or a nitroso radical. R$_1$ may also, for example, be chosen from chlorine, bromine and C$_1$–C$_4$ alkyl, C$_1$–C$_4$ hydroxyalkyl, C$_1$–C$_4$ aminoalkyl, C$_1$–C$_4$ alkoxy and C$_1$–C$_4$ hydroxyalkoxy radicals. Further, for example, R$_1$ may be chosen from methyl, hydroxymethyl, 2-hydroxyethyl, 1,2-dihydroxyethyl, methoxy, isopropyloxy and 2-hydroxyethoxy radicals.

The onium radicals Z may be chosen from radicals of formula (II)

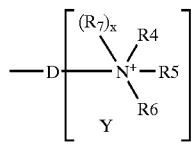

(II)

wherein

D is a linking arm chosen from a covalent bond and linear and branched C$_1$–C$_{14}$ alkylene chains which may be interrupted with at least one hetero atom chosen from oxygen, sulphur and nitrogen, and which may be substituted with at least one radical chosen from hydroxyl, C$_1$–C$_6$ alkoxy and amino radicals, and which may bear at least one ketone functional group;

R$_4$, R$_5$ and R$_6$, which may be identical or different, taken separately, are each chosen from C$_1$–C$_{15}$ alkyl radicals; C$_1$–C$_6$ monohydroxyalkyl radicals; C$_2$–C$_6$ polyhydroxyalkyl radicals; (C$_1$–C$_6$)alkoxy(C$_1$–C$_6$)alkyl radicals; aryl radicals; benzyl radicals; C$_1$–C$_6$ amidoalkyl radicals; tri(C$_1$–C$_6$)alkylsilane(C$_1$–C$_6$)alkyl radicals; C$_1$–C$_6$ aminoalkyl radicals; and C$_1$–C$_6$ aminoalkyl radicals wherein the amine is mono or disubstituted with a radical or two radicals, which may be identical or different, chosen from C$_1$–C$_4$ alkyl, (C$_1$–C$_6$) alkylcarbonyl, amido and (C$_1$–C$_6$)alkylsulphonyl radicals; with the proviso that when the linking arm D is a covalent bond then R$_4$ is chosen from aryl radicals; benzyl radicals; C$_1$–C$_6$ amidoalkyl radicals; tri(C$_1$–C$_6$)-alkylsilane(C$_1$–C$_6$)alkyl radicals; C$_1$–C$_6$ aminoalkyl radicals; C$_1$–C$_6$ aminoalkyl radicals wherein the amine is mono- or disubstituted with a radical or two radicals, which may be identical or different, chosen from C$_1$–C$_4$ alkyl, (C$_1$–C$_6$)alkylcarbonyl, amido and (C$_1$–C$_6$)alkylsulphonyl radicals, Two of the radicals chosen from R$_4$, R$_5$ and R$_6$ form, together with the nitrogen atom to which they are attached, a saturated carbon-based cationic ring chosen from 4-, 5-, 6- and 7-membered rings optionally comprising at least one hetero atom, for example, a cationic ring chosen from azetidine rings, pyrrolidine rings, piperidine rings, piperazine rings and morpholine rings, wherein the cationic ring may be substituted with at least one entity chosen from halogens, a hydroxyl radical, C$_1$–C$_6$ alkyl radicals, C$_1$–C$_6$ monohydroxyalkyl radicals, C$_2$–C$_6$ polyhydroxyalkyl radicals, C$_1$–C$_6$ alkoxy radicals, tri(C$_1$–C$_6$)alkylsilane(C$_1$–C$_6$) alkyl radicals, amido radicals, carboxyl radicals, (C$_1$–C$_6$)alkylcarbonyl radicals, thio (—SH) radicals, C$_1$–C$_6$ thioalkyl (—R—SH) radicals, (C$_1$–C$_6$)alkylthio radicals, amino radicals, and amino radicals mono-, di-, or tri-substituted with a radical or radicals, which may be identical or different, chosen from (C$_1$–C$_6$)alkyl, (C$_1$–C$_6$)alkylcarbonyl, amido and (C$_1$–C$_6$) alkylsulphonyl radicals;

R$_7$ is chosen from C$_1$–C$_6$ alkyl radicals; C$_1$–C$_6$ monohydroxyalkyl radicals; C$_2$–C$_6$ polyhydroxyalkyl radicals; aryl radicals; benzyl radicals; C$_1$–C$_6$ aminoalkyl radicals; C$_1$–C$_6$ aminoalkyl radicals wherein the amine may be mono- or disubstituted with a radical or two radicals, which may be identical or different, chosen from (C$_1$–C$_6$)alkyl, (C$_1$–C$_6$)alkylcarbonyl, amido and (C$_1$–C$_6$)alkylsulphonyl radicals; C$_1$–C$_6$ carboxyalkyl radicals; C$_1$–C$_6$ carbamylalkyl radicals; C$_1$–C$_6$ trifluoroalkyl radicals; tri(C$_1$–C$_6$)alkylsilane(C$_1$–C$_6$ )alkyl radicals; C$_1$–C$_6$ sulphonamidoalkyl radicals; (C$_1$–C$_6$) alkylcarboxy(C$_1$–C$_6$)alkyl radicals; (C$_1$–C$_6$) alkylsulphinyl(C$_1$–C$_6$)alkyl radicals; (C$_1$–C$_6$) alkylsulphonyl(C$_1$–C$_6$)alkyl radicals; (C$_1$–C$_6$) alkylcarbonyl(C$_1$–C$_6$)alkyl radicals; N-(C$_1$–C$_6$) alkylcarbamyl(C$_1$–C$_6$)alkyl radicals; and N-(C$_1$–C$_6$) alkylsulphonamido(C$_1$–C$_6$)alkyl radicals;

x is 0 or 1, when x=0, then the linking arm D is attached to the nitrogen atom bearing the radicals R$_4$, R$_5$, and R$_6$, when x=1, then two of the radicals chosen from R$_4$, R$_5$, and R$_6$ form, together with the nitrogen atom to which they are attached, a saturated ring chosen from 4-, 5-, 6- and 7-membered rings and the linking arm D is linked to a carbon atom of the saturated ring;

Y is a counter-ion.

In formula (II), when x is equal to 0, then $R_4$, $R_5$ and $R_6$, which may be identical or different, are each, for example, chosen from $C_1$–$C_6$ alkyl radicals, $C_1$–$C_4$ monohydroxyalkyl radicals, $C_2$–$C_4$ polyhydroxyalkyl radicals, $(C_1$–$C_6)$ alkoxy$(C_1$–$C_4)$alkyl radicals, $C_1$–$C_6$ amidoalkyl radicals, tri$(C_1$–$C_6)$alkylsilane$(C_1$–$C_6)$alkyl radicals, or $R_4$ and $R_5$ form, together with the nitrogen to which they are attached, a ring chosen from azetidine, pyrrolidine, piperidine, piperazine and morpholine rings, $R_6$ being chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine may be mono- or disubstituted with a radical or two radicals, chosen from $(C_1$–$C_6)$alkyl, $(C_1$–$C_6)$alkylcarbonyl, amido and $(C_1$–$C_6)$alkylsulphonyl radicals; $C_1$–$C_6$ carbamylalkyl radicals; tri$(C_1$–$C_6)$alkylsilane$(C_1$–$C_6)$alkly radicals; $(C_1$–$C_6)$alkylcarboxy$(C_1$–$C_6)$alkyl radicals; $(C_1$–$C_6)$ alkylcarbonyl$(C_1$–$C_6)$alkyl radicals; and N-$(C_1$–$C_6)$ alkylcarbamyl$(C_1$–$C_6)$alkyl radicals.

When x is equal to 1, then $R_7$ is, for example, chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine may be mono- or disubstituted with a radical or two radicals, which may be identical or different, chosen from $(C_1$–$C_6)$alkyl, $(C_1$–$C_6)$alkylcarbonyl, amido and $(C_1$–$C_6)$alkylsulphonyl radicals; $C_1$–$C_6$ carbamylalkyl radicals; tri$(C_1$–$C_6)$ alkylsilane$(C_1$–$C_6)$alkyl radicals; $(C_1$–$C_6)$alkylcarboxy-$(C_1$–$C_6)$alkyl radicals; $(C_1$–$C_6)$alkylcarbonyl$(C_1$–$C_6)$alkyl radicals; and N-$(C_1$–$C_6)$alkylcarbamyl$(C_1$–$C_6)$alkyl radicals; $R_4$ and $R_5$ form, together with the nitrogen to which they are attached, a ring chosen from azetidine, pyrrolidine, piperidine, piperazine and morpholine rings, $R_6$ being chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine may be mono- or disubstituted with a radical or two radicals, which may be identical or different, chosen from $(C_1$–$C_6)$alkyl, $(C_1$–$C_6)$alkylcarbonyl, amido and $(C_1$–$C_6)$alkylsulphonyl radicals; $C_1$–$C_6$ carbamylalkyl radicals; tri$(C_1$–$C_6)$alkylsilane$(C_1$–$C_6)$alkyl radicals; $(C_1$–$C_6)$alkylcarboxy$(C_1$–$C_6)$alkyl radicals; $(C_1$–$C_6)$ alkylcarbonyl$(C_1$–$C_6)$alkyl radicals; and N-$(C_1$–$C_6)$ alkylcarbamyl$(C_1$–$C_6)$alkyl radicals.

In formula (II), the linking arm D may, for example, be chosen from a covalent bond and an alkylene chain that may be substituted.

The onium radicals Z may be chosen from radicals of formula (III)

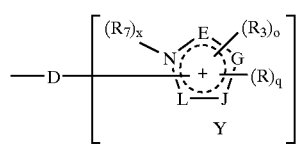
(III)

wherein

D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;

the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings, q is an integer ranging from 0 to 4;

o is an integer ranging from 0 to 3;

q+o is an integer ranging from 0 to 4;

R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri$(C_1$–$C_6)$ alkylsilane$(C_1$–$C_6)$alkyl radicals, amido radicals, carboxyl radicals, $C_1$–$C_6$ alkylcarbonyl radicals, thio radicals, $C_1$–$C_6$ thioalkyl radicals, $(C_1$–$C_6)$alkylthio radicals, amino radicals, amino radicals mono- or disubstituted with a radical or two radicals, which may be identical or different, chosen from $(C_1$–$C_6)$alkyl, $(C_1$–$C_6)$alkylcarbonyl, amido and $(C_1$–$C_6)$ alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri$(C_1$–$C_6)$ alkylsilane$(C_1$–$C_6)$alkyl radicals, $(C_1$–$C_6)$alkoxy $(C_1$–$C_6)$alkyl radicals, $C_1$–$C_6$ carbamylalkyl radicals, $(C_1$–$C_6)$alkylcarboxy$(C_1$–$C_6)$alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is substituted with at least one radical chosen from $(C_1$–$C_6)$alkyl, $(C_1$–$C_6)$alkylcarbonyl, amido and $(C_1$–$C_6)$alkylsulphonyl radicals; $C_1$–$C_6$ carboxyalkyl radicals; $C_1$–$C_6$ carbamylalkyl radicals; $C_1$–$C_6$ trifluoroalkyl radicals; tri$(C_1$–$C_6)$alkylsilane$(C_1$–$C_6)$alkyl radicals; $C_1$–$C_6$ sulphonamidoalkyl radicals; $(C_1$–$C_6)$ alkylcarboxy$(C_1$–$C_6)$alkyl radicals; $(C_1$–$C_6)$ alkylsulphinyl$(C_1$–$C_6)$alkyl radicals; $(C_1$–$C_6)$ alkylsulphonyl$(C_1$–$C_6)$alkyl radicals; $(C_1$–$C_6)$ alkylcarbonyl$(C_1$–$C_6)$alkyl radicals; N-$(C_1$–$C_6)$ alkylcarbamyl$(C_1$–$C_6)$alkyl radicals; and N-$(C_1$–$C_6)$ alkylsulphonamido$(C_1$–$C_6)$alkyl radicals;

x is 0 or 1 when x=0, the linking arm D is attached to the nitrogen atom, when x=1, the linking arm D is attached to one of the ring members chosen from E, G, J and L, Y is a counter-ion.

By way of example, the ring members E, G, J and L, together with the ring nitrogen, may form a ring chosen from pyrrole, imidazole, pyrazole, oxazole, thiazole and triazole rings. In one embodiment, the ring members E, G, J and L, together with the ring nitrogen, form an imidazole ring.

In another embodiment, the onium radicals Z are chosen from radicals of formula (III), wherein x is equal to 0 and the linking arm D is chosen from a covalent bond and an alkylene chain that may be substituted.

The onium radicals Z may be chosen from radicals of formula (IV)

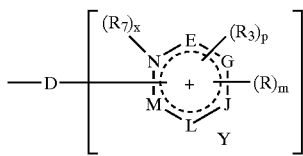

(IV)

wherein:

D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;

the ring members E, G, J, L and M, which may be identical or different, are each chosen from carbon, oxygen, sulphur and nitrogen atoms and, together with the ring nitrogen, form a ring chosen from pyridine, pyrimidine, pyrazine, triazine and pyridazine rings;

p is an integer ranging from 0 to 3;

m is an integer ranging from 0 to 5;

p+m is an integer ranging from 0 to 5;

R, which may be identical or different, is chosen from halogen atoms, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1 when x=0, the linking arm D is attached to the nitrogen atom, when x=1, the linking arm D is attached to one of the ring members chosen from E, G, J, L and M, Y is a counter-ion.

In one embodiment, the ring members E, G, J, L and M form, with the nitrogen of the ring, a ring chosen from pyridine and pyrimidine rings.

When x is equal to 0, then R is chosen, for example, from a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, $C_1$–$C_6$ alkylcarbonyl radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals, and $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals and $C_1$–$C_6$ carbamylalkyl radicals.

When x is equal to 1, $R_7$ is chosen, for example, from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl radicals, ($C_1$–$C_6$)alkylcarbonyl radicals, amido radicals and ($C_1$–$C_6$) alkylsulphonyl radicals; $C_1$–$C_6$ carbamylalkyl radicals; tri ($C_1$–$C_6$)alkylsilane($C_1$–$C_6$)alkyl radicals; ($C_1$–$C_6$) alkylcarbony($C_1$–$C_6$)alkyl radicals; and N-($C_1$–$C_6$) alkylcarbamyl($C_1$–$C_6$)alkyl radicals; R is chosen from a hydroxyl radical, $C_1$–$C_6$ alkyl radicals, $C_1$–$C_6$ monohydroxyalkyl radicals, $C_2$–$C_6$ polyhydroxyaklyl radicals, $C_1$–$C_6$ alkoxy radicals, tri($C_1$–$C_6$)alkylsilane($C_1$–$C_6$)alkyl radicals, amido radicals, $C_1$–$C_6$ alkylcarbonyl radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; and $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane ($C_1$–$C_6$)alkyl radicals, ($C_1$–$C_6$)alkoxy($C_1$–$C_6$)alkyl radicals and $C_1$–$C_6$ carbamylalkyl radicals.

In one embodiment, R, $R_7$ and $R_3$ are alkyl radicals that may be substituted.

The radical $R_2$ may also be chosen from onium radicals of formula —XP(O)(O—)OCH$_2$CH$_2$N$^+$(CH$_3$)$_3$ wherein X is chosen from oxygen and radicals —NR$_{11}$, wherein R$_{11}$ is chosen from hydrogen, $C_1$–$C_4$ alkyl radicals and hydroxyalkyl radicals.

In one embodiment, $R_2$ may also be chosen from guanidine radicals of formula —X—C=NR$_8$—NR$_9$R$_{10}$, wherein X is chosen from oxygen and a radical —NR$_{11}$, and R$_8$, R$_9$, R$_{10}$ and R$_{11}$, which may be identical or different, are each chosen from hydrogen, $C_1$–$C_4$ alkyl radicals, and hydroxyalkyl radicals. In another embodiment, X is chosen from radicals of —NR$_{11}$, R$_8$ is a hydrogen and R$_9$ and R$_{10}$, which may be identical or different, are each chosen from hydrogen and alkyl radicals, for example, a methyl radical.

The pKa of the guanidine radical $R_2$ is such that this substituent is present in cationic form (=NR$_8$H$^+$) under the standard conditions for the oxidation dyeing of hair.

As used herein, the counter-ion may be chosen from halogens such as bromine, chlorine, fluorine and iodine, hydroxides, citrates, succinates, tartrates, lactates, tosylates, mesylates, benzenesulphonates, acetates, a hydrogen sulphate, and $C_1$–$C_6$ alkyl sulphates such as methyl sulphate and ethyl sulphate.

The pyrrolidinyl-substituted para-phenylenediamine derivatives of formula (I) and the addition salts thereof may, for example, be chosen from:

| Formula | Nomenclature |
|---|---|
| 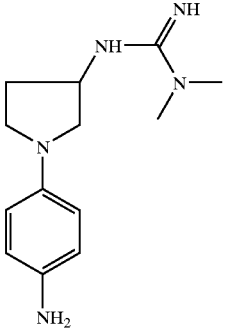 | N'-[1-(4-Amino-phenyl)-pyrrolidin-3-yl]-N,N-dimethyl-guanidine |
| 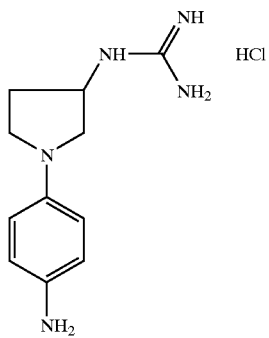 | N-[1-(4-Amino-phenyl)-pyrrolidin-3-yl]-guanidine |
| 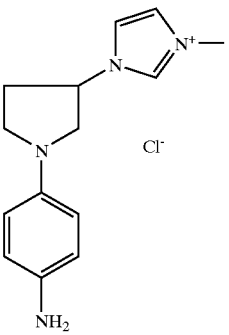 | 3-[1-(4-Amino-phenyl)-pyrrolidin-3-yl]-1-methyl-3H-imidazol-1-ium chloride |
| 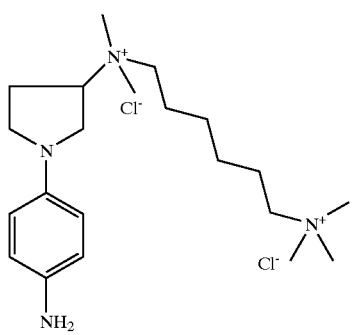 | [1-(4-Amino-phenyl)-pyrrolidin-3-yl]-(-trimethylammonium-hexyl)-dimethyl-ammoniumdichloride |

-continued

| Formula | Nomenclature |
|---|---|
| | [1-(4-Amino-phenyl)-pyrrolidin-3-yl]-dimethyl-(3-trimethylsilanyl-propyl)-ammonium chloride |
| | {2-[1-(4-Amino-phenyl)-pyrrolidin-3-yloxy]-ethyl}-trimethyl-ammonium chloride |
| | [1-(4-Amino-phenyl)-pyrrolidin-3-yl]-oxophosphorycholine |
| | 3-{3-[1-(4-Amino-phenyl)-pyrrolidin-3-yloxy]-propyl}-1-methyl-3H-imidazol-1-ium chloride |
| | 1-{2-[1-(4-Amino-phenyl)-pyrrolidin-3-yloxy]-ethyl}-1-methyl-pyrrolidinium chloride |

| Formula | Nomenclature |
|---|---|
| | 3-{3-[1-(5-trimethylsilanylethyl-4-Amino-3-trimethylsilanylethyl-phenyl)-pyrrolidin-3-yloxy]-propyl}-1-methyl-3H-imidazol-1-um chloride |
| | 1-{2-[1-(4-Amino-phenyl)-pyrrolidin-3-yloxy]-ethyl}-1-methyl-piperidinium chloride |
| | N-[1-(4-Amino-3-methyl-phenyl)-pyrrolidin-3-yl]-guanidine |
| | N'-[1-(4-Amino-3-methyl-phenyl)-pyrrolidin-3-yl]-N,N-dimethyl-guanidine |

-continued
| Formula | Nomenclature |
|---|---|
| 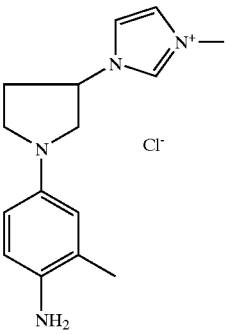 | 3-[1-(4-Amino-3-methyl-phenyl)-pyrrolidin-3-yl]-1-methyl-3H-imidazol-1-ium chloride |
| 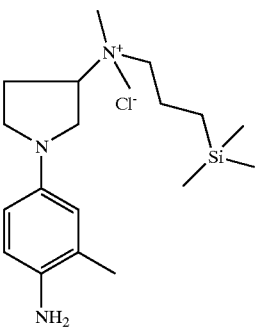 | [1-(4-Amino-3-methyl-phenyl)-pyrrolidin-3-yl]-dimethyl-(3-trimethylsilanyl-propyl ammonium chloride |
| 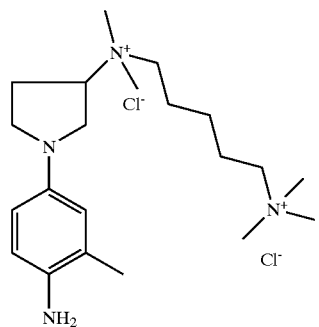 | [1-(4-Amino-3-methyl-phenyl)-pyrrolidin-3-yl]-(-trimethylammonium-hexyl)-dimethyl-ammonium dichloride |
| 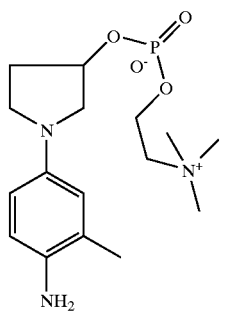 | [1-(4-Amino-3-methyl-phenyl)-pyrrolidin-3-yl]-oxophosphorycholine |

-continued

| Formula | Nomenclature |
|---|---|
| | {2-[1-(4-Amino-3-methyl-phenyl)-pyrrolidin-3-yloxy]-ethyl}-trimethyl-ammonium chloride |
| | 1-{2-[1-(4-Amino-3-methyl-phenyl)-pyrrolidin-3-yloxy]-ethyl}-1-methyl-pyrrolidinium chloride |
| | 3-{3-[1-(4-Amino-3-methyl-phenyl)-pyrrolidin-3-yloxy]-propyl}-1-methyl-3H-imidazol-1-um chloride |
| | 1-{2-[1-(4-Amino-3-methyl-phenyl)-pyrrolidin-3-yloxy]-ethyl}-1-methyl-piperidine |
| | 3-[1-(5-trimethylsilanylethyl-4-Amino-3-trimethylsilanylethyl-phenyl)-pyrrolidin-3-yl]-1-methyl-3H-imidazol-1-ium chloride |

-continued

| Formula | Nomenclature |
|---|---|
| | 3-[1-(4-Amino-3-trimethylsilanylethyl-phenyl)-pyrrolidin-3-yl]-1-methyl-3H-imidazol-1-ium chloride |
| | 3-{3-[1-(4-Amino-3-trimethylsilanylethyl-phenyl)-pyrrolidin-3-yloxy]-propyl}-1-methyl-3H-imidazol-1-ium chloride |
| | 1'(4-Amino-phenyl)-1-methyl-[1,3']bipyrrolidinyl-1-ium chloride |
| | 1'-(4-Amino-3-methyl-phenyl)-1-methyl-[1,3']bipyrrolidinyl-1-ium chloride |

-continued

| Formula | Nomenclature |
|---|---|
| | 3-{[1-(4-Amino-phenyl)-pyrrolidin-3-ylcarbamoyl]-methyl}-1-methyl-3H-imidazol-1-ium chloride |
| | 3-{[1-(4-Amino-3-methyl-phenyl)-pyrrolidin-3-ylcarbamoyl]-methyl}-1-methyl-3H-imidazol-1-ium chloride |
| | 3-[1-(4-Amino-phenyl)-pyrroldin-3-yl]-1-(3-trimethylsilanyl-propyl)-3H-imidazol-1-iumchloride |
| | 3-[1-(4-Amino-3-methyl-phenyl)-pyrrolidin-3-yl]-1-(3-trimethylsilanyl-propyl)-3H-imidazol-1-ium chloride |

| Formula | Nomenclature |
|---|---|
| 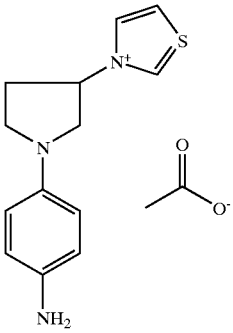 | 3-[1-(4-Amino-phenyl)-pyrrolidin-3-yl]-thiazol-3-ium Acetate |
| 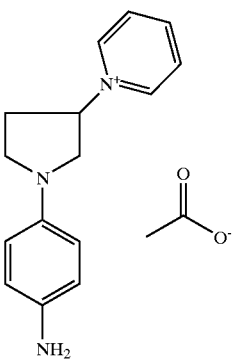 | 1-[1-(4-aminophenyl)pyrrolidin-3-yl]pyridinium Acetate |
| 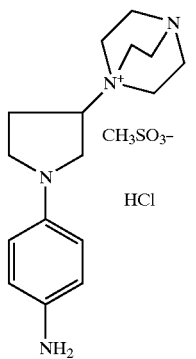 | 1-[1-(4-Amino-phenyl)-pyrrolidin-3-yl]-4-aza-1-azonia-bicyclo[2,2,2]octane; methanesulfonate hydrochloride |

The pyrrolidinyl-substituted para-phenylenediamine derivatives of formula (I) and addition salts thereof may, for example, be chosen from:

N'-[1-(4-Aminophenyl)pyrrolidin-3-yl]-N,N-dimethylguanidine;
N-[1-(4-Aminophenyl)pyrrolidin-3-yl]guanidine;
3-[1-(4-Aminophenyl)pyrrolidin-3-yl]-1-methyl-3H-imidazol-1-ium chloride;
[1-(4-Aminophenyl)pyrrolidin-3-yl]dimethyl-(3-trimethylsilanylpropyl)ammonium chloride;
N'-[1-(4-Amino-3-methylphenyl)pyrrolidin-3-yl]-N,N-dimethylguanidine;
N-[1-(4-Amino-3-methylphenyl)pyrrolidin-3-yl]guanidine;
3-[1-(4-Amino-3-methylphenyl)pyrrolidin-3-yl]-1-methyl-3H-imidazol-1-ium chloride;
[1-(4-Amino-3-methylphenyl)pyrrolidin-3-yl]dimethyl-(3-trimethylsilanylpropylammonium chloride;
3-[1-(4-Aminophenyl)pyrrolidin-3-yl]-1-(3-trimethylsilanylpropyl)-3H-imidazol-1-ium chloride;
3-[1-(4-Amino-3-methylphenyl)pyrrolidin-3-yl]-1-(3-trimethylsilanylpropyl)-3H-imidazol-1-ium chloride;
1'-(4-Aminophenyl)-1-methyl-[1,3']bipyrrolidinyl-1-ium chloride;
1'-(4-Amino-3-methylphenyl)-1-methyl-[1,3']bipyrrolidinyl-1-ium chloride;
3-{[1-(4-Aminophenyl)pyrrolidin-3-ylcarbamoyl]methyl}-1-methyl-3H-imidazol-1-ium chloride;
3-{[1-(4-Amino-3-methylphenyl)pyrrolidin-3-ylcarbamoyl]methyl}-1-methyl-3H-imidazol-1-ium chloride; and
1'-(4-amino-phenyl)-1-methyl-[1,3']bipyrrolidinyl-1-ium chloride.

According to one embodiment, the linking arm D comprises at least one phosphoryl radical, for example, at least one radical chosen from [1-(4-Amino-phenyl)-pyrrolidin-3-yl]-oxophosphorylcholine and [1-(4-Amino-3-methyl-phenyl)-pyrrolidin-3-yl]-oxophosphorylcholine.

The dye composition disclosed herein comprises, in a medium suitable for dyeing keratin fibers, such as human hair, at least one oxidation base chosen from pyrrolidinyl-substituted para-phenylenediamine derivatives of formula (I) and the addition salts thereof as defined above.

The at least one oxidation base may be present in an amount ranging, for example, from 0.001% to 10% by weight, relative to the total weight of the dye composition, further for example, from 0.005% to 6% by weight, relative to the total weight of the dyeing composition.

The dye composition disclosed herein may further comprise at least one coupler conventionally used for dyeing keratin fibers. The at least one coupler may, for example, be chosen from meta-phenylenediamines, meta-aminophenols, meta-diphenols, naphthalenic couplers and heterocyclic couplers, and the addition salts thereof.

The at least one coupler may, for example, be chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenze and 2,6-bis(β-hydroxyethylamino)toluene and the acid addition salts thereof.

In one embodiment, the at least one coupler is present in an amount ranging from 0.001% to 10% by weight, relative to the total weight of the dye composition, further for example, from 0.005% to 6% by weight, relative to the total weight of the dye composition.

In another embodiment, the dye composition may also comprise at least one additional oxidation base conventionally used in oxidation dyeing, other than those described above. The at least one additional oxidation base may, for example, be chosen from para-phenylenediamines other than those described above, such as bis(phenyl) alkylenediamines, para-aminophenols, bis-para-aminophenols, ortho-aminophenols and heterocyclic bases, and the addition salts thereof.

The para-phenylenediamines may, for example, be chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,β-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenyl-pyrrolidine, 2-thienyl-para-phenylenediamine, 2-β-hydroxyethylamino-5-aminotoluene and 3-hydroxy-1-(4'-aminophenyl)pyrrolidine, and the acid addition salts thereof.

The para-phenylenediamines may, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

The bis(phenyl)alkylenediamines may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4-aminophenyl)ethlyenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

The para-aminophenols may be chosen, for example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

The ortho-aminophenols may be chosen, for example, from 2-aminophenol, 2-amino-5-methylphenol, 2-amino-6-methylphenol and 5-acetamido-2-aminophenol, and the acid addition salts thereof.

The heterocyclic bases, may be chosen, for example, from pyridine derivatives, pyrimidine derivatives and pyrazole derivatives.

The pyridine derivatives may be chosen from compounds disclosed, for example, in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

The pyridine oxidation bases may also be chosen, for example, from 3-aminopyrazolo[1,5-a]pyridine oxidation bases and the addition salts thereof disclosed, for example, in Patent Application No. FR 2 801 308. For example, the pyridine oxidation bases may be chosen from pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-7-yl)(2-hydroxyethyl)amino]

ethanol; 2-[(3-aminopyrazolo[1,5-a]pyrid-7-yl)(2-hydroxyethyl)amino]ethanol; 3-aminopyrazolo-[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and the acid and base addition salts thereof.

The pyrimidine derivatives may be chosen, for example, from the compounds disclosed in Patent Nos. DE 2 359 399 and JP 88-169 571; JP 05 63 124; EP 0 770 375 and Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those disclosed in Patent Application FR-A-2 750 048 such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyridine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolypropylaminopyrazolo[1,5-a]pyrimidine, and the acid addition salts thereof and the tautomeric forms thereof, when a tautomeric equilibrium exists.

The pyrazole derivatives may be chosen from compounds disclosed in Patent Nos. DE 3 843 892 and DE 4 133 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The at least one additional oxidation base may be present in the dye composition in an amount ranging, for example, from 0.001% to 10% by weight, relative to the total weight of the dye composition, further for example, from 0.005% to 6% by weight, relative to the total weight of the composition.

The addition salts of the at least one oxidation base, of the at least one additional oxidation base, and of the at least one coupler may be chosen, for example, from the acid addition salts, such as the hydrochlorides, hydrobromides, sulphates, citrates, succinates, tartrates, lactates, tosylates, benzenesulphonates, phosphates and acetates, and the base addition salts, such as sodium hydroxide, potassium hydroxide, ammonia, amines and alkanolamines.

In another embodiment, the dye composition disclosed herein may also comprise at least one direct dye chosen, for example, from nitrobenzene dyes, azo direct dyes and methine direct dyes. The at least one direct dye may be of nonionic, anionic or cationic nature.

The medium suitable for dyeing, also known as the dye support, comprises water or a mixture of water and at least one organic solvent to dissolve the compounds that are not sufficiently soluble in water. The at least one organic solvent may, for example, be chosen from $C_1-C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol and phenoxyethanol.

The at least one organic solvent may be present in an amount ranging, for example, from 1% to 40% by weight, relative to the total weight of the dye composition, further for example, from 5% to 30% by weight, relative to the total weight of the dyeing composition.

In another embodiment, the dye composition may also comprise, for example, at least one adjuvant conventionally used in compositions for dyeing the hair. For example, the at least one adjuvant may be chosen from anionic, cationic, nonionic, amphoteric and zwitterionic surfactants, anionic, cationic, nonionic, amphoteric and zwitterionic polymers, inorganic and organic thickeners, for example, anionic, cationic, nonionic and amphoteric associative polymeric thickeners, antioxidants, penetration agents, sequestering agents, fragrances, buffers, dispersing agents, packaging agents, for example, volatile and non-volatile, modified and unmodified silicones, film-forming agents, ceramides, preserving agents and opacifiers.

The at least one adjuvant may be present in an amount ranging, for example, from 0.01% to 20% by weight, relative to the weight of the composition.

A person skilled in the art may choose at least one optional additional compound such that the advantageous properties intrinsically associated with the oxidation dye composition disclosed herein are not, or are not substantially, adversely affected by the addition envisaged.

The pH of the dye composition disclosed herein may range, for example, from 3 to 12, further for example, from 5 to 11. The pH may be adjusted to the desired value using, for example, at least one agent chosen from acidifying and basifying agents. The acidifying agents and the basifying agents may be chosen, for example, from those conventionally used in the dyeing of keratin fibers and standard buffer systems.

The acidifying agents may, for example, be chosen from inorganic and organic acids such as hydrochloric acid, orthophosphoric acid, sulphuric acid, carboxylic acids such as acetic acid, tartaric acid, citric acid and lactic acid, and sulphonic acids.

The basifying agents may, for example, be chosen from aqueous ammonia, alkaline carbonates, alkanolamines such as mono-, di- and triethanolamine and derivatives thereof, sodium hydroxide, potassium hydroxide and the compounds of formula (V) below:

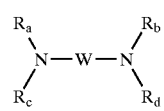

(V)

wherein W is chosen from propylene residues optionally substituted with at least one radical chosen from a hydroxyl radical and $C_1-C_4$ alkyl radicals; $R_a$, $R_b$, $R_c$ and $R_d$, which may be identical or different, are each chosen from hydrogen, $C_1-C_4$ alkyl radicals and $C_1-C_4$ hydroxyalkyl radicals.

The dye composition disclosed herein may be in various forms, such as in a form chosen from liquids, creams, gels, and any other form that may be suitable for dyeing keratin fibers, such as human hair.

Further disclosed herein is a process comprising applying the dye composition disclosed herein to keratin fibers, wherein the color may be developed using at least one oxidizing agent. The color may be developed, for example, at acidic, neutral or alkaline pH. The at least one oxidizing agent may be added to the dye composition disclosed herein at the time of use, or an oxidizing composition comprising at least one oxidizing agent may, be applied simultaneously or sequentially to the dye composition disclosed herein.

In one embodiment, the dye composition disclosed herein may be mixed, for example, at the time of use, with an oxidizing composition comprising, in a medium suitable for dyeing, at least one oxidizing agent. The at least one oxidizing agent is present in an amount that is sufficient to develop a coloration. The mixture obtained then may be applied to the keratin fibers. After an action time ranging from 3 to 50 minutes, for example, from 5 to 30 minutes, the keratin fibers may be rinsed, washed with shampoo, rinsed again and then dried.

The at least one oxidizing agent used for the oxidation dyeing of keratin fibers may be chosen, for example, from hydrogen peroxide, urea peroxide, alkali metal bromates, persalts such as perborates and persulphates, peracids and oxidase enzymes, such as peroxidases, 2-electron oxidoreductases such as uricases, and 4-electron oxygenases, such as laccases. In one embodiment, the at least one oxidizing agent is hydrogen peroxide.

The oxidizing composition may also comprise at least one adjuvant chosen from those conventionally used in compositions for dyeing the hair, such as those adjuvants defined above.

The pH of the oxidizing composition comprising the at least one oxidizing agent may be such that, after mixing with the dye composition, the pH of the resulting composition applied to the keratin fibers ranges, for example, from 3 to 12, further for example, from 5 to 11. The pH may be adjusted to the desired value using, for example, at least one agent chosen from acidifying and basifying agents. The acidifying and basifying agents may be chosen from those conventionally used in the dyeing of keratin fibers and standard buffer systems as defined above.

The ready-to-use composition that is finally applied to the keratin fibers may, for example, be in various forms, such as in a form chosen from liquids, creams and gels and any other form that is suitable for dyeing keratin fibers, such as human hair.

Further disclosed herein is a multi-compartment dyeing device or "kit", comprising a first compartment comprising the dye composition disclosed herein and a second compartment comprising the oxidizing composition. This device may, for example, be equipped with a means for applying the desired mixture to the hair, such as the devices disclosed in Patent No. FR-2 586 913.

Using this device, it is possible to dye keratin fibers using a process comprising mixing a dye composition comprising at least one oxidation base chosen from pyrrolidinyl-substituted para-phenylenediamine derivative of formula (I) and the addition salts thereof with at least one oxidizing agent, and applying the mixture obtained to the keratin fibers for a time that is sufficient to develop the desired coloration.

Even further disclosed herein are nitro pyrrolidinyl-substituted para-phenylenediamine derivatives of formula (I') and the addition salts thereof, such derivatives being intermediate compounds in the synthesis of pyrrolidinyl-substituted para-phenylenediamine derivatives of formula (I).

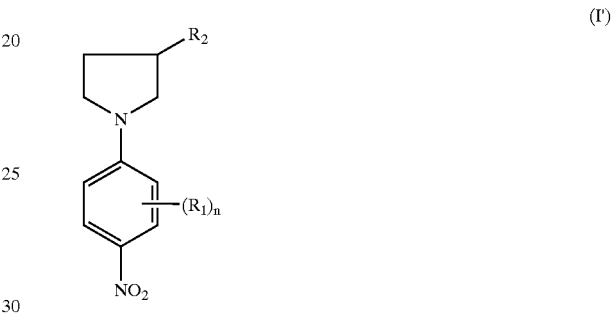

(I')

wherein $R_1$, n and R2 are previously defined herein.

The pyrrolidinyl-substituted para-phenylenediamine derivatives of formula (I) and the addition salts thereof as disclosed herein can be prepared by the application or adaptation of known methods. For example, they can be obtained by the adaptation of the methods disclosed below.

The examples that follow serve to illustrate the invention without, however, being limiting in nature.

EXAMPLES

Example 1

Synthesis of 1-methyl-3-[1-(4-aminophenyl)pyrrolidin-3-yl]-3H-imidazol-1-ium chloride hydrochloride

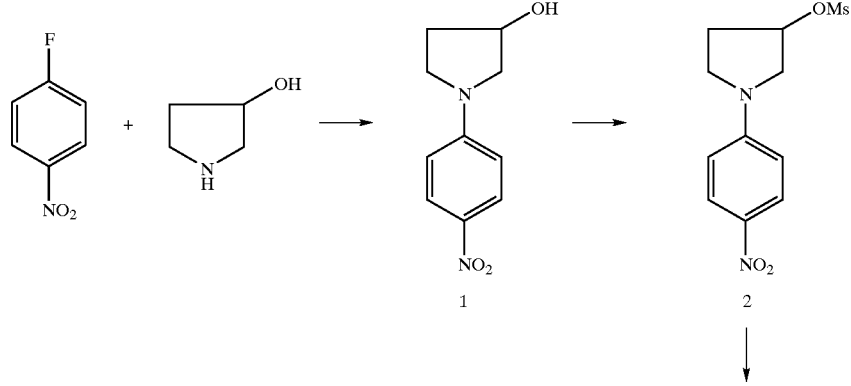

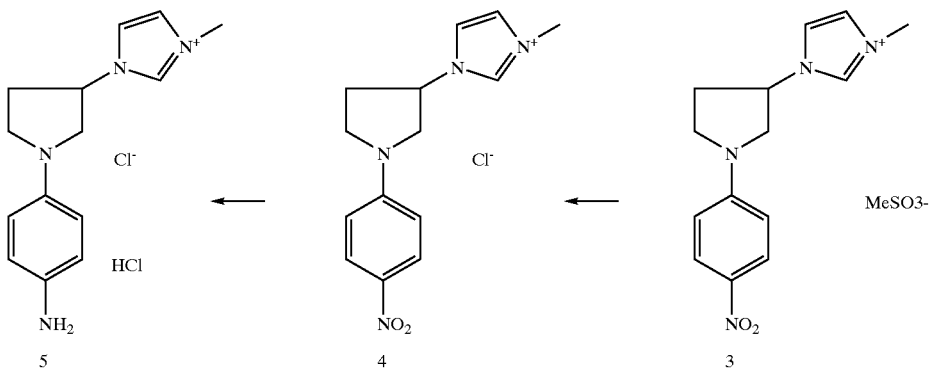

Synthesis of 1-(4-nitrophenyl)pyrrolidin-3-ol (1)

2 g of 1-fluoro-4-nitrobenzene (0.0155 mol), 1.3 g of sodium hydrogen carbonate (0.0155 mol) and 15 ml of a dioxane/water mixture (8/2) were placed in a three-necked flask. 1.35 g of 3-pyrrolidinol (0.0155 mol) was rapidly added to this mixture. The heterogeneous mixture was heated at reflux (87° C.) for 10 hours. The reaction mixture was then poured into ice-water; a yellow precipitate was obtained, which was filtered off and rinsed with water. After drying under vacuum in the presence of $P_2O_5$, 2.95 g of a yellow solid are obtained (97% yield).

$^1$H NMR (DMSO-$d_6$, 200 MHz, ppm) in accordance with the expected product: 8.04 (d, J=9 Hz, 2H); 6.58 (d, J=9 Hz, 2H); 5.06 (d, J=3.6 Hz, 1H); 4.41 (m, 1H); 3.45 (m, 3H); 3.20 (m, 1H); 2.04 (m, 2H).

| Elemental analysis: | | | | |
|---|---|---|---|---|
| % | C | H | N | O |
| Calculated | 57.89 | 5.81 | 13.45 | 23.05 |
| Found | 57.17 | 5.72 | 13.23 | 23.28 |

Synthesis of 1-(4-aminophenyl)pyrrolidin-3-yl methanesulphonate (2)

40 ml (0.516 mol) of mesyl chloride was added dropwise at 5° C. to 83.3 g (0.4 mol) of N-(4-nitrophenly)-3-hydroxypyrrolidine (1) dissolved in 625 ml of anhydrous THF and 72.7 ml (0.6 mol) of triethylamine. The mixture was allowed to return to room temperature and was then poured onto ice. After filtering off the precipitate by suction and drying, 109 g of yellow powder (2) was obtained.

Melting point: 203° C.

$^1$H NMR (400 MHz-DMSO) ppm 8.09 (d, 2H); 6.68 (d, 2H); 5.47 (m,1H); 3.77–3.48 (m, 4H); 3.28 (s, 3H); 2.35 (m, 2H).

ESI+MASS: m/z=287 [MH+].

Synthesis of 1-methyl-3-[1-(4-nitrophenyl)pyrrolidin-3-yl]-3H-imidazol-1-ium methanesulphonate (3)

23 g (0.08 mol) of 1-(4-nitrophenyl)pyrrolidin-3-yl methanesulphonate (2) was heated for 8 hours at 85° C. in 150 g of 1-methylimidazole (1.82 mol). This solution was stirred in 2 l of ethyl acetate to the point of crystallization. After filtration and drying, 24 g of yellow powder (3) was obtained.

$^1$H NMR (400 MHz-DMSO) ppm 9.44 (s, 1H); 8.29 (d, 2H); 8.07 (m, 1H); 7.96 (m, 1H); 6.91 (d, 2H); 5.48 (m, 1H); 4.16 (m, 1H); 4.02 (s, 3H) from 3.98 to 3.79 (m, 4H); 2.85 (m, 1H); 2.69 (m, 1H); 2.50 (s, 3H).

ESI+mass: m/z=273 [M+].

Synthesis of 1-methyl-3-[1-(4-nitrophenyl)pyrrolidin-3-yl]-3H-imidazol-1-ium chloride (4)

23 g (0.0624 mol) of 1-methyl-3-[1-(4-nitrophenyl) pyrrolidin-3-yl]-3H-imidazol-1-ium methanesulphonate (3) dissolved in 200 ml of water was stirred with 500 g of Amberlite IRA-402 ion-exchange resins for 14 hours; the resin was separated out by filtration and the filtrate was concentrated and then taken up in isopropanol. The yellow powder was recovered by filtration and then dried. 16.5 g of 1-methyl-3-[1-(4-nitrophenyl)pyrrolidin-3-yl]-3H-imidazol-1-ium chloride (4) was obtained.

$^1$H NMR (400 MHz-DMSO) ppm 9.35 (s, 1H); 8.11 (m, 2H); 8.90 (m, 1H); 7.78 (m, 1H); 6.71 (m, 2H); 5.31 (m, 1H); 4.37 (m, 1H); from 3.98 to 3.95 (m, 1H); 3.85 (s, 3H); from 3.83 to 3.69 (m, 4H); from 2.51 to 2.49 (m, 2H);

ESI+mass: m/z=307 [M+].

Synthesis of 1-methyl-3-[1-(4-aminophenyl)pyrrolidin-3-yl]-1H-imidazol-1-ium chloride hydrochloride (5)

16 g (0.0518 mol) of the preceding derivative (4) dissolved in 600 ml of ethanol was hydrogenated in the presence of palladium-on-charcoal under a hydrogen pressure of 8 bar. After filtering off the catalyst, the expected derivative (5) was isolated in the form of the hydrochloride.

$^1$H NMR (400 MHz-DMSO) ppm 8.86 (s, 1H); 7.59 (t, 1H); 7.54 (t, 1H); 7.41 (m, 2H); 6.89 (m, 2H); 5.33 (m, 1H); 3.97 (m, 3H); 3.85 (m, 2H); 3.71 (m, 1H); 3.50 (m, 1H); 2.76 (m, 1H); 2.51 (m, 1H);

ESI+mass: m/z=243 [M+].

Example 2

Synthesis of 1'-(4-Amino-phenyl)-1-methyl-[1,3']bipyrrolidinyl-1-ium chloride hydrochloride

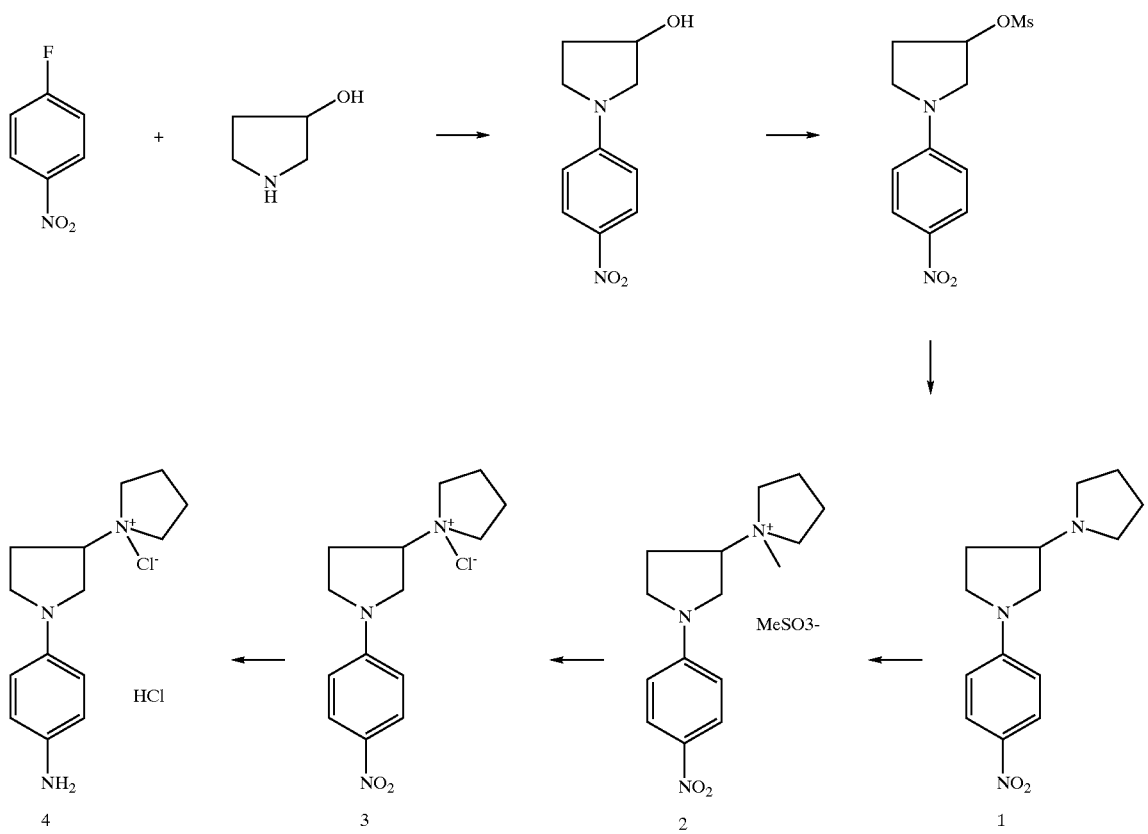

Synthesis of 1'-(4-Nitro-phenyl)-[1,3']bipyrrolidinyl (1)

5 g (0.0174 mole) of methanesulfonic acid 1-(4-nitro-phenyl)-pyrrolidin-3yl ester (2) were heated 2 hours at 85° C. in 30 ml of pyrrolidine. The mixture was then poured on ice water until crystallization occurred. After filtrating and drying, the obtained yellow powder was chromatographed with an eluent consisting of dichloromethane/methanol (98/2). 2.6 g of derivative (1) was thus obtained (yield 53%).

melting point=114° C.

RMN 1H (400 MHz, DMSO) ppm 8.04 (m, 2H); 6.61 (m, 2H); 3.60(m, 2H); 3.40(m, 1H); 3.24 (m, 1H); 2.86 (m,1H); 2.50 (m, 2H); 2.16 (m, 1H); 1.92 (m, 1H); 1.70 (m, 4H).

ESI+Mass: m/z=262(MH+)

Synthesis of 1-Methyl-1'-(4-nitro-phenyl)-[1,3']bipyrrolidinyl-1-ium; chloride (3)

24.8 g (0.095 mole) of 1'-(4-Nitro-phenyl)-[1,3']bipyrrolidinyl (1) were mixed with 330 ml of ethylacetate. 10 ml (0.105 mole) of dimethylsulfate were added and the mixture was heated at reflux for 4 hours. At ambient temperature, the yellow powder thus obtained was filtered off, washed with ethyl acetate and dried under vacuum. The ions were exchanged on Amberlite IRA-402 resin. 21 g of a yellow powder were obtained (3) (yield 75%).

RMN 1H (400 MHz, D2O) ppm 7.96 (m, 2H); 6.51 (m, 2H); 4.3 (m, 1H); 3.78–3.39 (m, 8H); 2.98 (s,3H); 2.97–2.42 (m, 2H); 2.16 (m, 4H).

ESI+Mass: m/z=276(M+)

Synthesis of 1'-(4-Amino-phenyl)-1-methyl-[1,3']bipyrrolidinyl-1-ium chloride, hydrochloride (4)

21 g (0.067 mole) of the preceding derivative (3) in 700 ml of ethanol was hydrogenated in presence of palladium on charcoal under hydrogen pressure of 10 bars; after filtration of the catalyst, the derivative (4) was isolated under hydrochloride form.

RMN 1H (400 MHz, DMSO) ppm 2,29 (m, 4H); 2,49 (m, 1H); 2,63 (m, 1H); 3,1 (s, 3H); 3,35 (m, 1H); 3,69 (m, 7H); 3,8 (dd, 1H); 4,42 (m, 1H); 6,86 (m, 2H); 7,35 (m, 2H).

ESI+Mass: m/z=246(M+)

Example 3

Synthesis of 3-[1-(4-Amino-3-methyl-phenyl)-pyrrolidin-3-yl]-1-methyl-3Himidazol-1-ium chloride hydrochloride

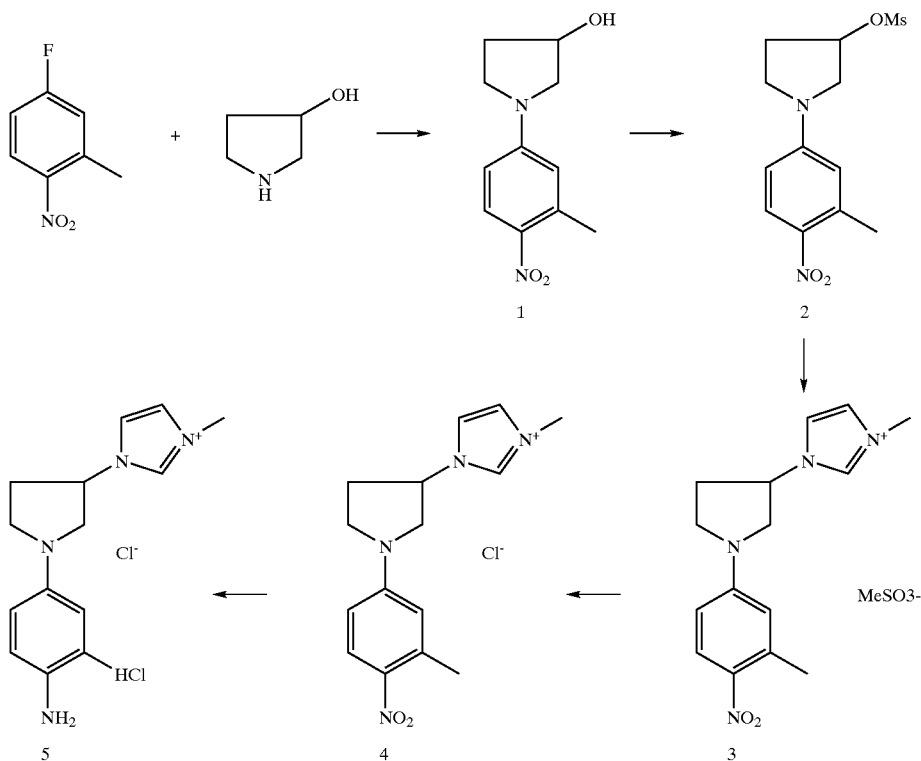

Synthesis of 1-(3-Methyl-4-nitro-phenyl)-pyrrolidin-3-ol (1)

In a three necked flask, 38.78 g of 5-fluoro-2-nitrotoluene (0.25 mol), 41.4 g of potassium carbonate (0.3 mol) and 200 ml of N-methylpyrrolidinone were mixed. 26.13 g of 3-pyrrolidinol (0.3 mol) were added to this mixture. The heterogeneous mixture was agitated at ambient temperature for 12 hours. The reacting mixture was then poured on ice water. A yellow powder was then obtained. The powder was then filtered off and rinsed with water. After drying under vacuum with $P_2O_5$, 55.56 g of a yellow solid were obtained (yield) (95%).

RMN 1H (400 MHz-DMSO) ppm 8.01 (d, 1H); 6.50–6.46 (m, 2H); 5.04 (m, 1H); 4.42 (m, 1H) 3.50–3.42 (m, 3H); 3.24–3.21 (m, 1H); 2.56 (s, 3H); 2.15–1.90 (m, 2H).

Synthesis of 1-(3-methyl-4-nitro-phenyl)-pyrrolidin-3-yl methane sulfonic ester (2)

35.56 g (0.16 mole) of 1-(3-Methyl-4-nitro-phenyl)-pyrrolidin-3-ol (1) in 500 ml of anhydrous THF and 29 ml (0.24 mole) of triethylamine were mixed drop to drop with 16 ml (0.21 mole) of mesyl chloride at 5° C.

At ambient temperature, the mixture was agitated for 1 hour then poured on ice water. After filtering and drying, 48 g of a yellow powder were obtained (2).

RMN 1H (400 MHz-DMSO) ppm 7.98–7.95 (m, 1H); 6.50–6.47 (m, 2H); 5.4 (m, 1H); 3.64–3.39 (m, 4H); 3.21 (s, 3H); 2.50 (s, 3H); 2.27–2.24 (m, 2H).

Synthesis of 1-Methyl-3-[1-(3-methyl-4-nitro-phenyl)-pyrrolidin-3-yl]-3H-imidazol-1-ium methanesulfonate (3)

6 g (0.02 mole) of 1-(3-methyl-4-nitro-phenyl)-pyrrolidin-3-yl methane sulfonic ester (2) were heated 12 hours at 90° C. in 30 ml of 1-methylimidazole. The solution was agitated in 2 l of ethylacetate until crystallization. After filtering off and drying, 6.6 g of a yellow powder were obtained (3).

RMN 1H (400 MHz-DMSO) ppm 8.07 (s, 1H); 7.72 (m, 1H); 7.43 (s, 1H); 7.42 (m, 1H); 6.28–6.23 (m, 2H); 5.16 (m, 1H); 3.81–3.77 (m, 4H); 3.67–3.43 (m, 3H); 2.68 (s, 3H); 2.59 (m 1H); 2.35 (m, 1H); 2.28 (s, 3H).

ESI+Mass: m/z=287[M+]

Synthesis of 1-Methyl-3-[1-(3-methyl-4-nitro-phenyl)-pyrrolidin-3-yl]-3H-imidazol-1-ium chloride (4)

6.5 g (0.017 mole) of 1-Methyl-3-[1-(3-methyl-4-nitro-phenyl)-pyrrolidin-3-yl]-3H-imidazol-1-ium methanesulfonate (3) in 200 ml of water were agitated with 200 g of an ion-exchange resin Amberlite IRA-402 for 12 hours. The resin was separated by filtration, the filtrate was concentrated then mixed with isopropanol. A yellow powder was then obtained after filtering off and drying (3.4 g).

RMN 1H (400 MHz-DMSO) ppm 8.72 (s, 1H); 7.65 (m, 1H); 7.43 (s, 1H); 7.37 (m, 1H); 6.22–6.17 (m, 2H); 5.16 (m, 1H); 3.78 (m, 4H); 3.64–3.40 (m, 3H); 2.60–2.56 (m, 1H); 2.40–2.37 (m, 1H); 2.23 (s, 3H).

ESI+Mass: m/z=287[M+]

Synthesis of 1-methyl-3-[1-(3-methyl-4-amino-phenyl)-pyrrolidin-3-yl]-3H-imidazol-1-ium chloride, hydrochloride (5)

3.2 g (0.01 mole) of derivative (4) in 300 ml of ethanol were hydrogenated in the presence of palladium on charcoal under hydrogen pressure of 9 bars. The catalyst was removed by filtration. The derivative (5) was isolated under chloride form.

RMN 1H (400 MHz-DMSO) ppm 7,35 (m, 2H); 6,86 (m, 2H); 4,42 (m, 1H); 3,8 (dd, 1H); 3,69 (m, 7H); 3,35 (m, 1H); 3,1 (s, 3H); 2,63 (m,1H); 2,49 (m, 1H); 2,29 (m, 4H).

ESI+Mass: m/z=257[M+]

Example 4

Synthesis of N-[1-(4-aminophenyl)pyrrolidin-3-yl] guanidine trihydrochloride

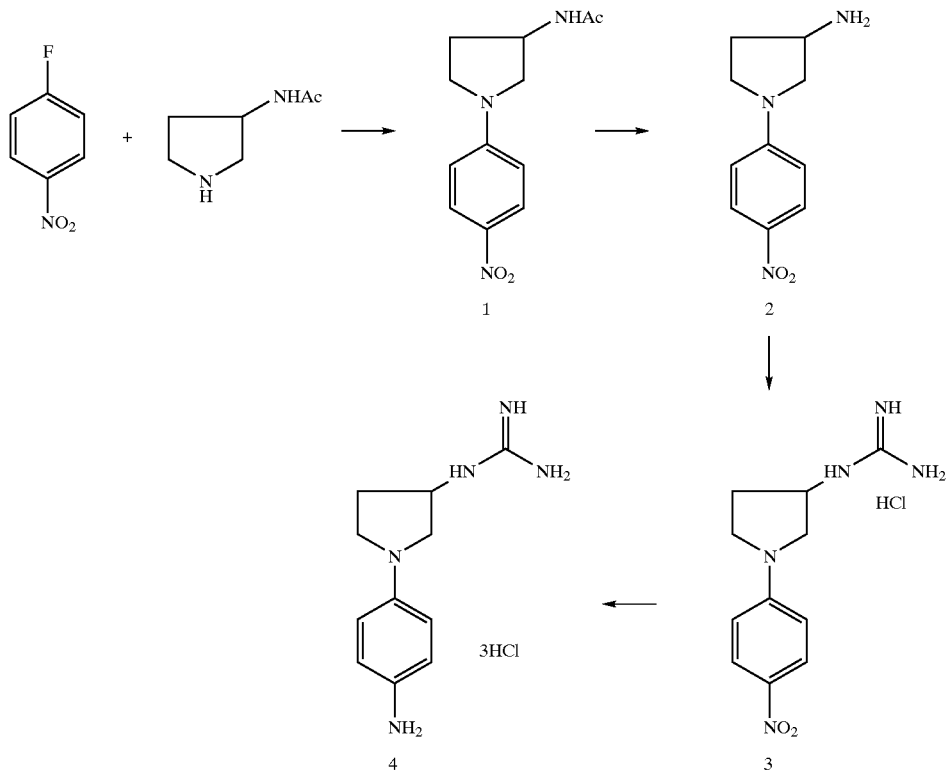

Synthesis of N-[1-(4-nitrophenyl)pyrrolidin-3-yl]acetamide (1)

After dissolving 56.4 g of 1-fluoro-4-nitrobenzene (0.4 mol) and 51.2 g of 3-acetamidopyrrolidine (0.4 mol) in 400 ml of NMP, 66.4 g of potassium carbonate (0.48 mol) were added under a nitrogen atmosphere and the mixture was heated at 100° C. for 18 hours. The reaction medium was allowed to cool and was then poured into 2 l of water. The yellow precipitate formed was filtered off, washed with water and then dried in a vacuum oven over $P_2O_5$. 100 g (100%) of N-[1-(4-nitrophenyl)pyrrolidin-3-yl]acetamide (1) was thus obtained in the form of a yellow solid.

Synthesis of 1-(4-nitrophenyl)pyrrolidin-4-ylamine (2)

100 g (0.4 mol) of N-[1-(4-nitrophenyl)pyrrolidin-3-yl] acetamide (1) was placed in suspension in a solution containing 300 ml of 37% hydrochloric acid and 660 ml of water in a 2 l three-necked flask. The reaction medium was heated at 90° C. for 7 hours 45 minutes. After cooling, the medium was neutralized gently with 300 ml of aqueous 35% sodium hydroxide (pH=8 approximately). The resulting solid was subsequently filtered off and then washed with water until the washing waters were neutral. The product was then dried under vacuum over $P_2O_5$. 74 g (89%) of 1-(4-nitrophenyl)pyrrolidin-4-ylamine (2) was thus obtained in the form of a yellow solid.

Synthesis of N-[1-(4-nitrophenyl)pyrrolidin-3-yl]guanidine (3)

2.07 g (0.01 mol) of [1-(4-nitrophenyl)pyrrolidin-3-yl] amine (2) was heated to 90° C. in 10 ml of DMF. 1.32 g (0.0009 mol) of 1-amidinopyrazole monohydrochloride was added slowly to the reaction medium. The mixture was heated for 8 hours. A yellow solid was thus precipitated. The solid thus obtained was filtered off, washed with ethanol and dried under vacuum to give 2 g of a yellow powder (3) (70%).

$^1$H NMR (400 MHz, DMSO) ppm 8.08 (m, 2H), 6.66 (m, 2H), 4.34 (m, 1H), 3.72 (m, 2H), 3.56 (m, 1H), 3.48 (m, 1H), 3.33 (m, 1H), 2.31 (m, 1H), 2.02 (m, 1H).

ESI+mass: m/z=250 (MH+).

Synthesis of N-[1-(4-aminophenyl)pyrrolidin-3-yl] guanidine trihydrochloride (4)

1.8 g (0.063 mol) of the preceding derivative (3) dissolved in 50 ml of ethanol and 550 ml of water were hydrogenated in the presence of palladium-on-charcoal under a hydrogen pressure of 8 bar; after filtering off the catalyst, the expected derivative (4) was isolated in the form of the hydrochloride (60%).

$^1$H NMR (400 MHz, DMSO) ppm 7.52 (m, 2H), 7.31 (m, 2H), 4.53 (m,1H), 3.94 (dd, 1H), 3.84 (m, 1H), 3.72 (m, 2H), 2.64 (m, 1H), 2.28 (m, 1H).

ESI+mass: m/z=220 (MH+).

Example 5

3-[1-(4-Amino-phenyl)-pyrrolidin-3-yl]-thiazol-3-ium Acetate

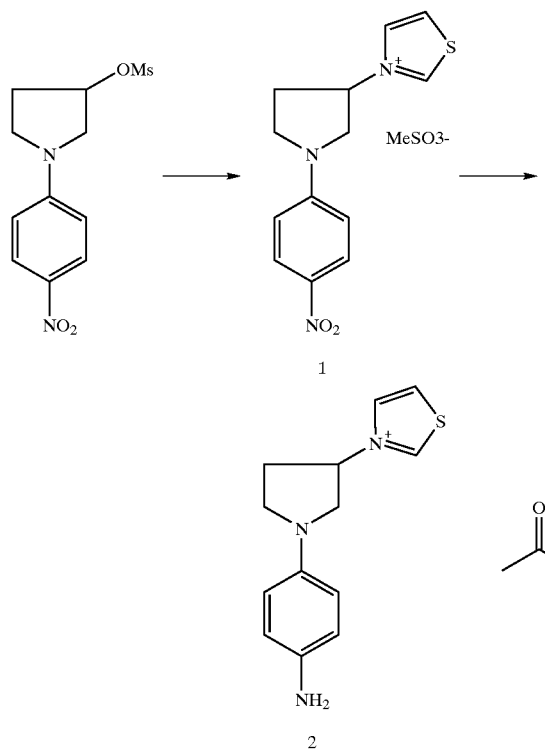

Example 6

1-[1-(4-aminophenyl)pyrrolidin-3-yl]pyridinium acetate

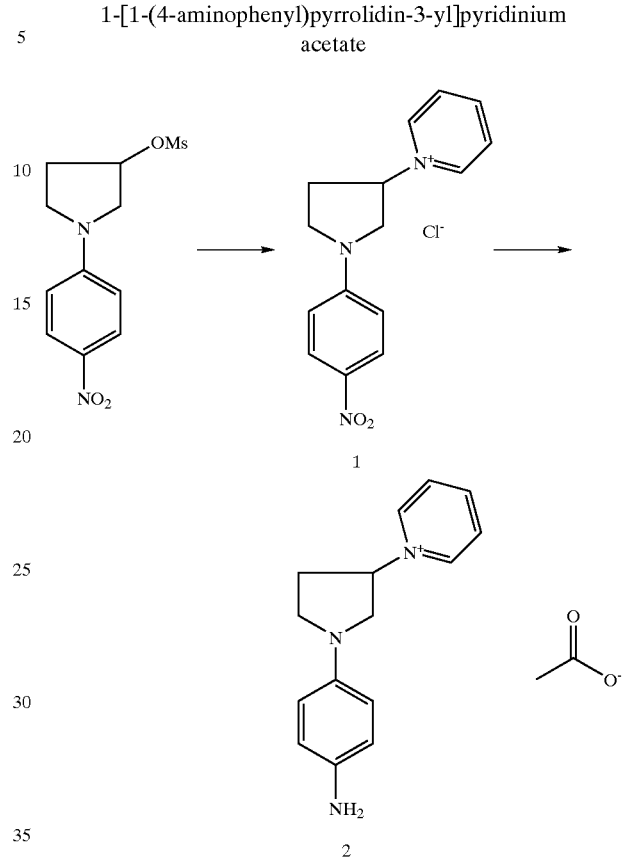

Synthesis of 3-[1-(4-nitrophenyl)pyrrolidin-3-yl]-1,3-thiazol-3-ium methanesulfonate (1)

1.14 g of 1-(4-nitrophenyl)pyrrolidin-3-yl methanesulfonate (0.004 mol), 0.01 g of sodium iodate and 5 g (0.059 mol) of thiazole were placed in a three-necked flask. The heterogeneous mixtures was heated at 110° C. for 18 hours. The reaction mixture was then poured into 100 ml of ethylacetate; a yellow precipitate was then obtained which was filtered off and rinsed with water. After drying under vacuum in the presence of $P_2O_5$, 1 g of a yellow solid was obtained. The obtained yellow solid was then recrystallized in isopropanol.

RMN 1H (400 MHz-DMSO) ppm) 10,26 (dd, 1H); 8,64 (dd, 1H); 8,41 (dd 1H); 8,12 (m ,2H); 6,74 (m, 2H); 5,72 (m, 1H); 4,05 (dd, 1H); 3,95 (dd, 1H); 3,76 (m, 1H ); 3,62 (m, 1H); 2,76 (m, 1H); 2,6 (m, 1H); 2,31 (s, 3H).

ESI+Mass: m/z=270[M+].

Synthesis of 3-[1-(4-Amino-phenyl)-pyrrolidin-3-yl]-thiazol-3-ium acetate (2)

After reducing with zinc/acetic acid, 1-[1-(4-aminophenyl)pyrrolidin-3-yl]thyazolium chloride was obtained.

ESI+Mass: m/z=246[M+].

Synthesis of 1-[1-(4-Nitro-phenyl)-pyrrolidin-3-yl]-pyridinium chloride (1)

7 g of 1-(4-nitrophenyl)pyrrolidin-3-yl methanesulfonate (0.0244 mol) and 60 ml of pyridin were placed in a three-necked flask. The mixture was heated at 100° C. for 16 hours. The precipitate was filtered off. After washing with ether and drying, 8.5 g of a yellow powder was obtained. The powder was solubilized in 200 ml of water, the solution was then passed through a IRA402 resin. After evaporating and drying, 5.4 g of 1-[1-(4-nitrophenyl)pyrrolidin-3-yl] pyridinium chloride was obtained. (1)

RMN 1H (400 MHz-DMSO) ppm 9,26 (m, 2H); 8,67 (m, 1H); 8,2 (m, 2H); 8,1 (m, 2H); 6,74 (m, 1H); 5,86 (m, 1H); 4,03 (dd, 1H); 3,84 (m, 1H); 3,62 (m, 1H); 2,84 (m, 1H); 2,67 (m, 1H).

ESI+Mass: m/z=270[M+].

Synthesis of 1-[1-(4-Amino-phenyl)-pyrrolidin-3-yl]-pyridinium acetate (2)

After reducing with zinc/acetic acid, 1-[1-(4-Amino-phenyl)-pyrrolidin-3-yl]-pyridinium acetate was obtained. (2)

ESI+Mass: m/z=240[M+].

Example 7

1-[1-(4-Amino-phenyl)-pyrrolidin-3-yl]-4-aza-1-azonia-bicyclo [2,2,2]octane; methanesulfonate; hydrochloride

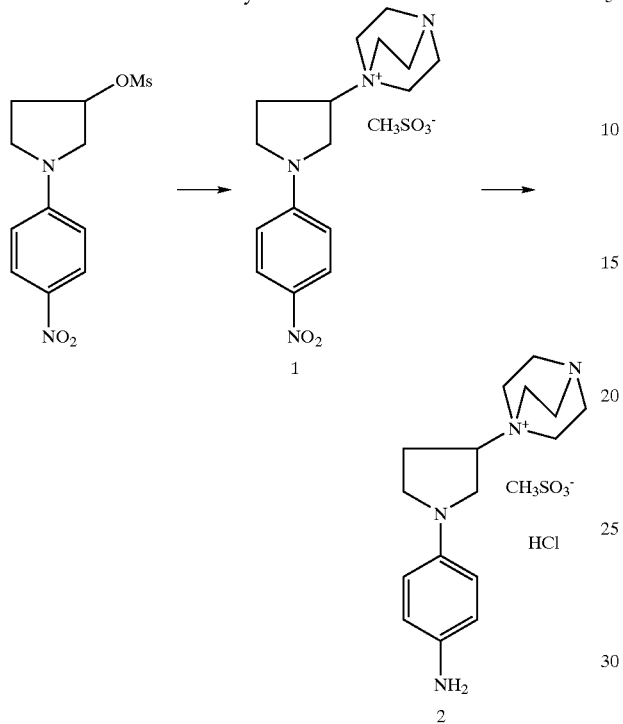

Synthesis of 1-[1-(4-nitrophenyl)pyrrolidin-3-yl]-4-aza-1-azoniabicyclo[2,2,2]octane; methanesulfonate 4.3 g of 1-(4-nitrophenyl)pyrrolidin-3-yl methanesulfonate (0.015 mol), 15 ml of methylethylacetone and 0.56 g (0.005 mol) of 1,4 diazabicyclo-2,2,2-octane were placed in a three-necked flask. The heterogeneous mixture was heated at 95° C. for 10 hours. The reaction mixture was then poured into 150 ml of water; the mixture was filtered off, the aqueous phase was extracted with butanol then concentrated; 0.8 g of a yellow powder was thus obtained after drying corresponding to 1-[1-(4-nitrophenyl)pyrrolidin-3-yl]-4-aza-1-azoniabicyclo[2,2,2]octane; methanesulfonate (1).

RMN 1H (400 MHz-DMSO) ppm 8,14 (d, 2H); 6,72 (d, 2H); 3,67–4,26 (m, 4H); 3,41 (m, 7H); 3,06 (m, 6H); 2,35–2,56 (m, 4H); 2,30 (s, 3H).

ESI+Mass: m/z=303[M+].

Synthesis of 1-[1-(4-Amino-phenyl)-pyrrolidin-3-yl]-4-aza-1-azonia-bicyclo[2,2,2]octane; methanesulfonate; hydrochloride 0.180 g of 1-[1-(4-nitrophenyl)pyrrolidin-3-yl]-4-aza-1-azoniabicyclo[2,2,2]octane; methanesulfonate was hydrogenated under hydrogen pressure of 10 bars in the presence of palladium-on-charcoal in ethanol. After filtrating off the catalyst, the expected derivative (2) was isolated under the hydrochloride form.

RMN 1H (400 MHz-D2O) ppm 7,35 (m, 2H); 6,88 (m, 2H); 4,6 (m, 1H); 4,11 (t, 6H); 4,02 (m, 2H); 3,96 (t, 6H); 3,74 (m, 2H); 2,8 (s, 3H); 2,66 (m, 2H).

ESI+Mass: m/z=373[M+].

Example 8

[1-(4-amino-phenyl)-pyrrolidin-3-yl]-oxophosphorylcholine derivative

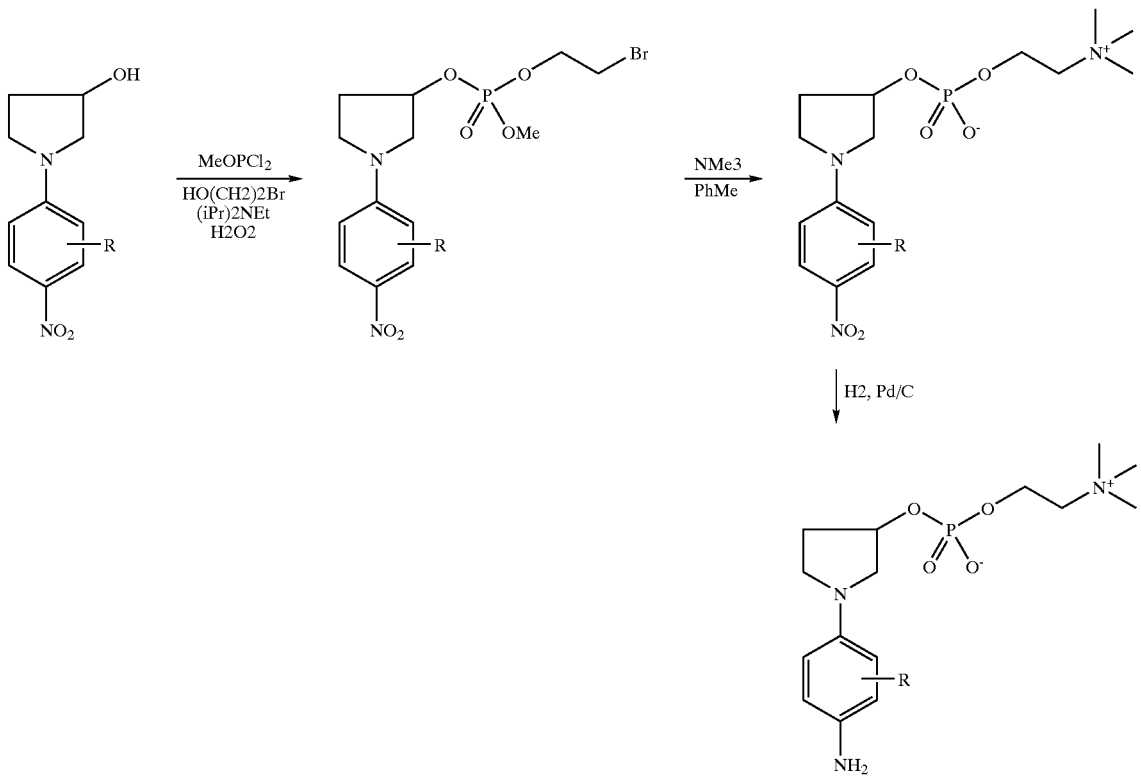

The synthesis of 1-(4-amino-phenyl)-pyrrolidin-3-yl]-oxophosphorylcholine derivatives was carried out from 1-(4-Nitro-phenyl)-pyrrolidin-3-ol compound under the protocol disclosed in S. F. Martin, *J. Org. Chem.* 1994, 59, 4805–4820.

DYEING EXAMPLES

Examples 1 to 20 of Dyeing Composition in an Alkaline Medium

The following compositions 1 to 20 were prepared. The amounts of each base and coupler are listed in moles ($1 \times 10^{-3}$ moles) relative to the total composition.

| Examples | 1 | 2 | 3 | 4 | 5 | 6 | 7 | 8 | 9 | 10 | 11 |
|---|---|---|---|---|---|---|---|---|---|---|---|
| N-[1-(4-Amino-phenyl)-pyrrolidin-3-yl]-guaninidine trihydrochloride (base) (mol) | $10^{-3}$ | $10^{-3}$ | $10^{-3}$ | $10^{-3}$ | — | — | — | — | — | — | — |
| 1'-(4-Amino-phenyl)-1-methyl-[1,3']bipyrrolidinyl-1-ium hydrochloride (base) (mol) | — | — | — | — | $10^{-3}$ | $10^{-3}$ | $10^{-3}$ | — | — | — | — |
| 3-[1-(4-Amino-3-methyl-phenyl)-pyrrolidin-3-yl]-1-methyl-3Himidazol-1-ium chloride hydrochloride (base) (mol) | — | — | — | — | — | — | — | $10^{-3}$ | $10^{-3}$ | $10^{-3}$ | $10^{-3}$ |
| 2-(2,4-Diamino-phenoxy)-ethanol, dihydrochloride (coupler) (mol) | $10^{-3}$ | — | — | — | $10^{-3}$ | — | — | $10^{-3}$ | — | — | — |
| 3-Amino-2-chloro-6-methyl-phenol, hydrochloride (coupler)(mol) | — | $10^{-3}$ | — | — | — | $10^{-3}$ | — | — | $10^{-3}$ | — | — |
| 3,6-Dimethyl-1H-pyrazolo[5,1-c][1,2,4]triazole (coupler) (mol) | — | — | $10^{-3}$ | — | — | — | $10^{-3}$ | — | — | $10^{-3}$ | — |
| 2-methyl-5-aminophenol (coupler)(mol) | — | — | — | $10^{-3}$ | — | — | — | — | — | — | $10^{-3}$ |
| Dyeing medium(1) | (*) | (*) | (*) | (*) | (*) | (*) | (*) | (*) | (*) | (*) | (*) |
| Demineralized water q.s. (g) | 100 | 100 | 100 | 100 | 100 | 100 | 100 | 100 | 100 | 100 | 100 |

| Examples | 12 | 13 | 14 | 15 | 16 | 17 | 18 | 19 | 20 |
|---|---|---|---|---|---|---|---|---|---|
| 1-[1-(4-Amino-phenyl)-pyrrolidin-3-yl]-4-aza-1-azonia-bicyclo[2,2,2]octane methanesulfonate hydrochlorite (base) (mol) | $10^{-3}$ | $10^{-3}$ | $10^{-3}$ | — | — | — | — | — | — |
| 3-[1-(4-Amino-phenyl)-pyrrolidin-3-yl]-thiazol-3-ium acetate (base) (mol) | — | — | — | $10^{-3}$ | $10^{-3}$ | $10^{-3}$ | — | — | — |
| 1-[1-(4-aminophenyl)pyrrolidin-3-yl]pyridinium acetate (base) (mol) | — | — | — | — | — | — | $10^{-3}$ | $10^{-3}$ | $10^{-3}$ |
| 2-(2,4-Diamino-phenoxy)-ethanol hydrochloride (coupler) (mol) | $10^{-3}$ | — | — | $10^{-3}$ | — | — | $10^{-3}$ | — | — |
| 3-Amino-2-chloro-6-methyl-phenol hydrochloride (coupler) (mol) | — | $10^{-3}$ | — | — | $10^{-3}$ | — | — | $10^{-3}$ | — |
| 3,6-Dimethyl-1H-pyrazolo[5,1-c][1,2,4]triazole (coupler) (mol) | — | — | $10^{-3}$ | — | — | $10^{-3}$ | — | — | $10^{-3}$ |

| -continued | | | | | | | | | |
|---|---|---|---|---|---|---|---|---|---|
| 2-methyl-5-aminophenol (coupler) | — | — | — | — | — | — | — | — | — |
| Dyeing medium (1) | (*) | (*) | (*) | (*) | (*) | (*) | (*) | (*) | (*) |
| Demineralized water q.s (g) | 100 | 100 | 100 | 100 | 100 | 100 | 100 | 100 | 100 |

| | |
|---|---|
| ethanol at 96° | 20.8 g |
| sodium metabisulfite in aqueous solution 35% | 0.23 g A.M. |
| diethylene-triamine-pentaacetic acid pentasodic salt in 40% aqueous solution | 0.48 g A.M. |
| $C_8$–$C_{10}$ alkylpolyglucoside in 60% aqueous solution | 3.6 g A.M. |
| benzylic alcohol | 2.0 g |
| Polyethylene glycol 8 EO | 3.0 g |
| $NH_4Cl$ | 4.32 g |
| Aqueous ammonia comprising 20% of $NH_3$ | 2.94 g |

At the time of use, the composition was mixed with an equal weight of 20-volumes aqueous hydrogen peroxide solution (6% by weight). The final pH was 9.5.

Each mixture was applied on locks of grey hair comprising 90% of white hairs. After an action of time of 30 minutes, the locks were rinsed, washed with a standard shampoo, rinsed again and dried.

The following results were obtained.

| Examples | 1 | 2 | 3 | 4 | 5 | 6 |
|---|---|---|---|---|---|---|
| Obtained glint | Violet blue | Blue violet | Chromatic Red Violet | Blue Violet | Violet blue | Violet blue |
| Examples | 7 | 8 | 9 | 10 | 11 | |
| Obtained glint | Chromatic red violet | Violet blue | violet | Chromatic red violet | Red Violet | |
| Examples | 12 | 13 | 14 | 15 | 16 | |
| Obtained glint | blue | violet | Chromatic red violet | blue | Blue Violet | |
| Examples | 17 | 18 | 19 | 20 | | |
| Obtained glint | Chromatic red violet | blue | violet | Chromatic red violet | | |

Examples 21 to 46 of Dyeing Composition in an Acid Medium

The following compositions 21 to 46 were prepared:

| Examples | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|
| N-[1-(4-Amino-phenyl)-pyrrolidin-3-yl]-guaninidine trihydrochloride (base) (mol) | $10^{-3}$ | $10^{-3}$ | $10^{-3}$ | $10^{-3}$ | $10^{-3}$ | $10^{-3}$ | — | — | — | — | — | — | — | — | — |
| 1'-(4-Amino-phenyl)-1-methyl-[1,3']bipyrrolidinyl-1-ium hydrochloride (base) (mol) | — | — | — | — | — | — | $10^{-3}$ | $10^{-3}$ | $10^{-3}$ | $10^{-3}$ | — | — | — | — | — |
| 3-[1-(4-Amino-3-methyl-phenyl)-pyrrolidin-3-yl]-1-methyl-3Himidazol-1-ium chloride hydrochloride(base) (mol) | — | — | — | — | — | — | — | — | — | — | $10^{-3}$ | $10^{-3}$ | $10^{-3}$ | $10^{-3}$ | $10^{-3}$ |
| 2-(2,4-Diamino-phenoxy)-ethanol dihydrochloride (coupler) (mol) | $10^{-3}$ | — | — | — | — | — | $10^{-3}$ | — | — | $10^{-3}$ | — | — | — | — | — |
| 3-Amino-2-chloro-6-methyl-phenol hydrochloride (coupler) (mol) | — | $10^{-3}$ | — | — | — | — | — | $10^{-3}$ | — | — | $10^{-3}$ | — | — | — | — |
| 2-methyl-5-aminophenol (coupler) (mol) | — | — | $10^{-3}$ | — | — | — | — | $10^{-3}$ | — | — | — | $10^{-3}$ | — | — | — |

-continued

| | | | | | | | | | | | | | | | |
|---|---|---|---|---|---|---|---|---|---|---|---|---|---|---|---|
| 2-Amino-pyridin-3-ol (coupler) (mol) | — | — | — | $10^{-3}$ | — | — | — | — | — | $10^{-3}$ | — | — | — | $10^{-3}$ | — |
| 3,6-Dimethyl-1H-pyrazolo[5,1-c][1,2,4]triazole (coupler) (mol) | — | — | — | — | $10^{-3}$ | — | — | — | — | — | — | — | — | — | — |
| 6-Hydroxy-1-H-indole (coupler)(mol) | — | — | — | — | — | $10^{-3}$ | — | — | — | — | — | — | — | — | $10^{-3}$ |
| Dyeing support (2) | (*) | (*) | (*) | (*) | (*) | (*) | (*) | (*) | (*) | (*) | (*) | (*) | (*) | (*) | (*) |
| Demineralized water q.s. (g) | 100 | 100 | 100 | 100 | 100 | 100 | 100 | 100 | 100 | 100 | 100 | 100 | 100 | 100 | 100 |

| Examples | 36 | 37 | 38 | 39 | 40 | 41 | 42 | 43 | 44 | 45 | 46 |
|---|---|---|---|---|---|---|---|---|---|---|---|
| 1-[1-(4-Amino-phenyl)-pyrrolidin-3-yl]-4-aza-1-azonia-bicyclo[2,2,2]octane methanesulfonate hydrochloride (base) mol | $10^{-3}$ | $10^{-3}$ | $10^{-3}$ | $10^{-3}$ | $10^{-3}$ | — | — | — | — | — | — |
| 3-[1-(4-Amino-phenyl)-pyrrolidin-3-yl]-thiazol-3-ium acetate (base) (mol) | — | — | — | — | — | $10^{-3}$ | $10^{-3}$ | $10^{-3}$ | $10^{-3}$ | — | — |
| 1-[1-(4-aminophenyl)pyrrolidin-3-yl]pyridinium acetate(base) (mol) | — | — | — | — | — | — | — | — | — | $10^{-3}$ | $10^{-3}$ |
| 2-(2,4-Diamino-phenoxy)-ethanol dihydrochloride (coupler) (mol) | $10^{-3}$ | — | — | — | — | $10^{-3}$ | — | — | — | $10^{-3}$ | — |
| 3-Amino-2-chloro-6-methyl-phenol hydrochloride (coupler) (mol) | — | $10^{-3}$ | — | — | — | — | $10^{-3}$ | — | — | — | $10^{-3}$ |
| 2-methyl-5-aminophenol (coupler) (mol) | — | — | $10^{-3}$ | — | — | — | — | $10^{-3}$ | — | — | — |
| 2-Amino-pyridin-3-ol (coupler) (mol) | — | — | — | $10^{-3}$ | — | — | — | — | — | — | — |
| 3,6-Dimethyl-1H pyrazolo[5,1-c][1,2,4]triazole (coupler) (mol) | — | — | — | — | — | — | — | — | — | — | — |
| 6-Hydroxy-1-H-indole (coupler) (mol) | — | — | — | — | $10^{-3}$ | — | — | — | $10^{-3}$ | — | — |
| Dyeing medium (2) | (*) | (*) | (*) | (*) | (*) | (*) | (*) | (*) | (*) | (*) | (*) |
| Demineralized water q.s. (g) | 100 | 100 | 100 | 100 | 100 | 100 | 100 | 100 | 100 | 100 | 100 |

(*) Dyeing medium (2) pH 7

| | |
|---|---|
| Ethanol 96° | 20.8 g |
| Sodium metabisulfite in aqueous solution at 35% | 0.23 g A.M. |
| diethylene-triamine-pentaacetic acid pentasodic salt in an aqueous solution at 40% | 0.48 g A.M. |
| $C_8$–$C_{10}$ alkyl polyglucoside in aqueous solution at 60% | 3.6 g A.M. |
| benzylic alcohol | 2.0 g |
| Polyethylene glycol at 8 EO | 3.0 g |
| $Na_2HPO_4$ | 0.28 g |
| $KH_2PO_4$ | 0.46 g |

At the time of use, the composition was mixed with an equal weight of 20-volumes aqueous hydrogen peroxide solution (6% by weight). The final pH was 9.5.

Each mixture was applied on locks of grey hair comprising 90% white hairs. After an action of time of 30 minutes, the locks were rinsed, washed with a standard shampoo, rinsed again and dried.

The following results were obtained.

| Examples | 21 | 22 | 23 | 24 | 25 | 26 |
|---|---|---|---|---|---|---|
| Obtained glint | Violet Blue | Blue Violet | Blue Violet | Brown violet | Red Violet | Brown Violet |

-continued

| Examples | 27 | 28 | 29 | 30 | 31 | 32 |
|---|---|---|---|---|---|---|
| Obtained glint | Violet blue | violet | Red Violet | Brown Violet | Violet blue | violet |
| Examples | 33 | 34 | 35 | 36 | 37 | 38 |
| Obtained glint | Red Violet | Brown Violet | Brown Violet | blue | violet | Red Violet |
| Examples | 39 | 40 | 41 | 42 | 43 | 44 |
| Obtained glint | Brown grey | Brown grey | blue | violet | Red Violet | Brown grey |
| | | | | Examples | 45 | 46 |
| | | | | Obtained glint | blue | violet |

What is claimed is:

1. A compound chosen from pyrrolidinyl-substituted para-phenylenediamine derivatives of formula (I) and the addition salts thereof:

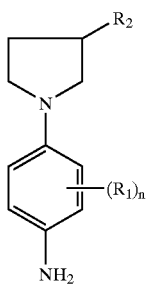

(I)

wherein:

n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains, wherein at least one carbon atom may be replaced with an entity chosen from an oxygen atom, a nitrogen atom, a silicon atom, a sulphur atom, and a $SO_2$ radical; with the proviso that the radical $R_1$ does not comprise a peroxide bond, a diazo radical, a nitro radical or a nitroso radical, $R_2$ is chosen from onium radicals Z and radicals —X—C=$NR_8$—$NR_9R_{10}$, wherein X is chosen from oxygen and —$NR_{11}$ radicals; $R_8$, $R_9$, $R_{10}$ and $R_{11}$, which may be identical or different, are each chosen from hydrogen, $C_1$–$C_4$ alkyl radicals and $C_1$–$C_4$ hydroxyalkyl radicals;

the onium radicals Z are chosen from radicals of formulae (II), (III), and (IV):

formula (II):

(II)

wherein

D is a linking arm chosen from a covalent bond and linear and branched $C_1$–$C_{14}$ alkylene chains which may be interrupted with at least one hetero atom chosen from oxygen, sulphur and nitrogen, and which may be substituted with at least one radical chosen from hydroxyl, $C_1$–$C_6$ alkoxy and amino radicals, and which may bear at least one ketone functional group;

$R_4$, $R_5$ and $R_6$, which may be identical or different, taken separately, are each chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$) alkylcarbonyl, amido and ($C_1$–$C_6$)alkylsulphonyl radicals; with the proviso that when the linking arm D is a covalent bond then $R_4$ is chosen from aryl radicals; benzyl radicals; $C_1$–$C_6$ amidoalkyl radicals; tri($C_1$–$C_6$) alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals, Two of the radicals chosen from $R_4$, $R_5$ and $R_6$ form, together with the nitrogen atom to which they are attached, a saturated carbon-based cationic ring chosen from 4-, 5-, 6- and 7-membered rings optionally comprising at least one hetero atom, wherein the cationic ring may be substituted with at least one entity chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri ($C_1$–$C_6$)alkylsilane($C_1$–$C_6$)alkyl radicals, amido radicals, carboxyl radicals, ($C_1$–$C_6$)alkylcarbonyl radicals, thio radicals, $C_1$–$C_6$ thioalkyl radicals, ($C_1$–$C_6$)alkylthio radicals, amino radicals, and amino radicals mono- di- or tri-substituted with a radical or radicals, which may be identical or different, chosen from ($C_1$–$C_6$)alkyl, ($C_1$–$C_6$)alkylcarbonyl, amido and ($C_1$–$C_6$)alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$)

alkylsulphinyl($C_1$–$C_6$)alkyl radicals; ($C_1$–$C_6$) alkylsulphonyl($C_1$–$C_6$)alkyl radicals; ($C_1$–$C_6$) alkylcarbonyl($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1,
 when x=0, then the linking arm D is attached to the nitrogen atom bearing the radicals $R_4$, $R_5$, and $R_6$,
 when x=1, then two of the radicals chosen from $R_4$, $R_5$, and $R_6$ form, together with the nitrogen atom to which they are attached, a saturated ring chosen from 5-, 6- and 7-membered rings and the linking arm D is linked to a carbon atom of the saturated ring; and Y is a counter-ion;

formula (III):

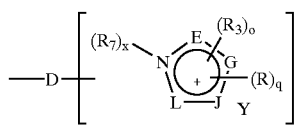

(III)

wherein
 D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;
 the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings,
 q is an integer ranging from 0 to 4;
 o is an integer ranging from 0 to 3;
 q+o is an integer ranging from 0 to 4;
 R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$) alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$) alkylsulphonyl radicals; $C_1$–$C_6$ monohydroxyalkyl radicals and $C_2$–$C_6$ polyhydroxyalkyl radicals; it being understood that the radical R is borne by a carbon atom,
 $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$) alkylsilane($C_1$–$C_6$)alkyl radicals, ($C_1$–$C_6$)alkoxy ($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom,
 $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–C6 carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylcarboxy($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1
 when x=0, the linking arm D is attached to the nitrogen atom,
 when x=1, the linking arm D is attached to one of the ring members chosen from E, G, J and L, and Y is a counter-ion;

formula (IV):

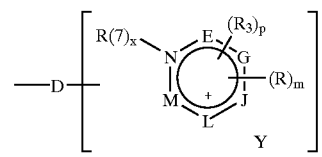

(IV)

wherein:
 D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;
 the ring members E, G, J, L and M, which may be identical or different, are each chosen from carbon, oxygen, sulphur and nitrogen atoms and form, together with the ring nitrogen, a ring chosen from pyridine, pyrimidine, pyrazine, triazine and pyridazine rings;
 p is an integer ranging from 0 to 3;
 m is an integer ranging from 0 to 5;
 p+m is an integer ranging from 0 to 5;
 R is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom,
 $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$) alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom,
 $R_7$ is chosen from $C_1$–$C_6$ alkyl radicals; $C_1$–$C_6$ monohydroxyalkyl radicals; $C_2$–$C_6$ polyhydroxyalkyl radicals;

aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1 when x=0, the linking arm D is attached to the nitrogen atom, when x=1, the linking arm D is attached to one of the ring members chosen from E, G, J, L and M, and Y is a counter-ion.

2. The compound according to claim 1, wherein, in formula (I), n is equal to 0.

3. The compound according to claim 1, wherein, in formula (I), n is equal to 1 and $R_1$ is chosen from halogens and from saturated and unsaturated, aliphatic and alicyclic $C_1$–$C_6$ hydrocarbon-based chains in which at least one carbon atom may be replaced with an entity chosen from an oxygen atom, a nitrogen atom, a silicon atom, a sulphur atom and an $SO_2$ group; with the proviso that the radical $R_1$ does not comprise a peroxide bond, a diazo radical, a nitro radical or a nitroso radical.

4. The compound according to claim 1, wherein, in formula (I), $R_1$ is chosen from chlorine, bromine and $C_1$–$C_4$ alkyl, $C_1$–$C_4$ hydroxyalkyl, $C_1$–$C_4$ aminoalkyl, $C_1$–$C_4$ alkoxy and $C_1$–$C_4$ hydroxyalkoxy radicals.

5. The compound according to claim 4, wherein $R_1$ is chosen from methyl, hydroxymethyl, 2-hydroxyethyl, 1,2-dihydroxyethyl, methoxy, isopropyloxy and 2-hydroxyethoxy radicals.

6. The compound according to claim 1, wherein, in formula (II):

x is equal to 0, and $R_4$, $R_5$ and $R_6$, which may be identical or different, taken separately, are each chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_1$–$C_4$)alkyl radicals, $C_1$–$C_6$ amidoalkyl radicals, and tri($C_1$–$C_6$)alkyl radicals, or $R_4$ and $R_5$ form, together with the nitrogen to which they are, attached, a ring chosen from azetidine, pyrrolidine, piperidine, piperazine and morpholine rings, and the $R_6$ is chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N-($C_1$–$C_6$)alkylcarbamyl($C_1$–$C_6$)alkyl radicals.

7. The compound according to claim 1, wherein, in formula (II):

x is equal to 1, $R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N-($C_1$–$C_6$)alkylcarbamyl($C_1$–$C_6$)alkyl radicals, $R_4$ and $R_5$ form, together with the nitrogen to which they are attached, a ring chosen from azetidine, pyrrolidine, piperidine, piperazine and morpholine rings, and the $R_6$ is chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N-($C_1$–$C_6$)alkylcarbamyl($C_1$–$C_6$)alkly radicals.

8. The compound according to claim 1, wherein the linking arm D is chosen from a covalent bond and an alkylene, chain that may be substituted.

9. The compound according to claim 1, wherein, in formula (III), the ring members E, G, J and L, together with the ring nitrogen, form a ring chosen from pyrrole, imidazole, pyrazole, oxazole, thiazole and triazole rings.

10. The compound according to claim 9, wherein the ring members E, G, J and L, together with the ring nitrogen, form an imidazole ring.

11. The compound according to claim 1, wherein, in formula (III), x is equal to 0 and the linking arm D is chosen from a covalent bond and an alkylene chain that is substituted.

12. The compound according to claim 1, wherein, in formula (IV), the ring members E, G, J, L and M form, with the ring nitrogen, a ring chosen from pyridine and pyrimidine rings.

13. The compound according to claim 1, wherein, in formula (IV):

x is equal to 0, and

R is chosen from a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, $C_1$–$C_6$ alkylcarbonyl radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals, and $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals and $C_1$–$C_6$ carbamylalkyl radicals.

14. The compound according to claim 1, wherein, in formula (IV):

x is equal to 1, $R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl radicals, ($C_1$–$C_6$) alkylcarbonyl radicals, amido radicals and ($C_1$–$C_6$) alkylsulphonyl radicals; $C_1$–$C_6$ carbamylalkyl radicals; tri($C_1$–$C_6$)alkylsilane($C_1$–$C_6$)alkyl radicals; ($C_1$–$C_6$) alkylcarbonyl($C_1$–$C_6$)alkyl radicals; and N-($C_1$–$C_6$) alkylcarbamyl($C_1$–$C_6$)alkyl radicals;

R is chosen from a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$) alkylsilane($C_1$–$C_6$)alkyl radicals, amido radicals, $C_1$–$C_6$ alkylcarbonyl radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; and $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$) alkoxy($C_1$–$C_6$)alkyl radicals and $C_1$–$C_6$ carbamylalkyl radicals.

15. The compound according to claim 1, wherein, in formula (III) or (IV), R, $R_7$ and $R_3$ are alkyl radicals that may be substituted.

16. The compound according to claim 1, wherein, in formula (I), $R_2$ is a radical —X—C=$NR_8$—$NR_9R_{10}$, wherein X is chosen from oxygen and a radical —$NR_{11}$; $R_8$, $R_9$, $R_{10}$ and $R_{11}$, which may be identical or different, are each chosen from hydrogen, $C_1$–$C_4$ alkyl radicals and hydroxyalkyl radicals.

17. The compound according to claim 16, wherein X is a radical —$NR_{11}$, $R_8$ is a hydrogen, and $R_9$ and $R_{10}$, which may be identical or different, are each chosen from hydrogen and alkyl radicals.

18. The compound according to claim 1, wherein, in formula (I), the $R_2$ is chosen from radicals —XP(O)(O—) $OCH_2CH_2N^+(CH_3)_3$ wherein X is chosen from oxygen and radicals —$NR_{11}$, wherein $R_{11}$ is chosen from hydrogen, $C_1$–$C_4$ alkyl radicals and hydroxyalkyl radicals.

19. The compound according to claim 1, wherein said compound is chosen from:

N'-[1-(4-Aminophenyl)pyrrolidin-3-yl]-N,N-dimethylguanidine,

N-[1-(4-Aminophenyl)pyrrolidin-3-yl]guanidine,

3-[1-(4-Aminophenyl)pyrrolidin-3-yl]-1-methyl-3H-imidazol-1-ium chloride,

[1-(4-Aminophenyl)pyrrolidin-3-yl]dimethyl-(3-trimethylsilanylpropyl)ammonium chloride, N'-[1-(4-Amino-3-methylphenyl)pyrrolidin-3-yl]-N,N-dimethylguanidine, N-[1-(4-Amino-3-methylphenyl)pyrrolidin-3-yl]guanidine, 3-[1-(4-Amino-3-methylphenyl)pyrrolidin-3-yl]-1-methyl-3H-imidazol-1-ium chloride,

[1-(4-Amino-3-methylphenyl)pyrrolidin-3-yl]dimethyl-(3-trimethylsilanylpropyl)ammonium chloride, 3-[1-(4-Aminophenyl)pyrrolidin-3-yl]-1-(3-trimethylsilanylpropyl)-3H-imidazol-1-ium chloride, 3-[1-(4-Amino-3-methylphenyl)pyrrolidin-3-yl]-1-(3-trimethylsilanylpropyl)-3H-imidazol-1-ium chloride, 1'-(4-Aminophenyl)-1-methyl-[1,3']bipyrrolidinyl-1-ium chloride, 1'-(4-Amino-3-methylphenyl)-1-methyl-[1,3'] bipyrrolidinyl-1-ium chloride, 3-{[1-(4-Aminophenyl)pyrrolidin-3-ylcarbamoyl] methyl}-1-methyl-3H-imidazol-1-ium chloride, 3-{[1-(4-Amino-3-methylphenyl)pyrrolidin-3-ylcarbamoyl]methyl}-1-methyl-3H-imidazol-1-ium chloride, and 1'-(4-amino-phenyl)-1-methyl-[1,3']bipyrrolidinyl-1-ium chloride.

20. The compound according to claim 19, wherein said compound is chosen from 1-methyl-3-[1-(4-aminophenyl) pyrrolidin-3-yl]-3H-imidazol-1-ium chloride hydrochloride; N-[1-(4-aminophenyl)pyrrolidin-3-yl]guanidine trihydrochloride, and 1'-(4-amino-phenyl)-1-methyl-[1,3'] bipyrrolidinyl-1-ium chloride.

21. The compound according to claim 1, wherein the linking arm D comprises a phosphoryl radical.

22. The compound according to claim 21, wherein the linking arm D is chosen from [1-(4-Amino-phenyl)-pyrrolidin-3-yl]-oxophosphorylcholine and [1-(4-Amino-3-methylphenyl)-pyrrolidine-3yl]-oxophosphorylcholine.

23. A dye composition comprising at least one oxidation base chosen from pyrrolidinyl-substituted paraphenylenediamine derivatives of formula (I) and the addition salts thereof:

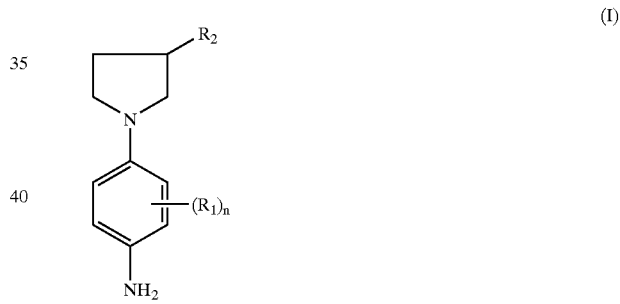

(I)

wherein:

n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains wherein at least one carbon atom may be replaced with an entity chosen from an oxygen atom, a nitrogen atom, a silicon atom, a sulphur atom, and a $SO_2$ radical with the proviso that the radical $R_1$ does not comprise a peroxide bond, a diazo radical, a nitro radical or a nitroso radical, $R_2$ is chosen from onium radicals Z and radicals —X—C=$NR_8$—$NR_9R_{10}$, wherein the X is chosen from oxygen and —$NR_{11}$ radicals; $R_8$, $R_9$, $R_{10}$ and $R_{11}$, which may be identical or different, are each chosen from hydrogen, $C_1$–$C_4$ alkyl radicals and $C_1$–$C_4$ hydroxyalkyl radicals;

the onium radicals Z are chosen from radicals of formulae (II), (III), and (IV):

formula (II):

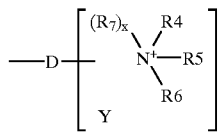

(II)

wherein

D is a linking arm chosen from a covalent bond and linear and branched $C_1$–$C_{14}$ alkylene chains which may be interrupted with at least one hetero atom chosen from oxygen, sulphur and nitrogen, and which may be substituted with at least one radical chosen from hydroxyl, $C_1$–$C_6$ alkoxy and amino radicals, and which may bear at least one ketone functional group;

$R_4$, $R_5$ and $R_6$, which may be identical or different, taken separately, are each chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$) alkylcarbonyl, amido and ($C_1$–$C_6$)alkylsulphonyl radicals; with the proviso that when the linking arm D is a covalent bond then $R_4$ is chosen from aryl radicals; benzyl radicals; $C_1$–$C_6$ amidoalkyl radicals; tri($C_1$–$C_6$) alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals;

Two of the radicals chosen from $R_4$, $R_5$ and $R_6$ form, together with the nitrogen atom to which they are attached, a saturated carbon-based cationic ring chosen from 4-, 5-, 6- and 7-membered rings optionally comprising at least one hetero atom wherein the cationic ring may be substituted with at least one entity chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri ($C_1$–$C_6$)alkylsilane($C_1$–$C_6$)alkyl radicals, amido radicals, carboxyl radicals, ($C_1$–$C_6$)alkylcarbonyl radicals, thio radicals, $C_1$–$C_6$ thioalkyl radicals, ($C_1$–$C_6$)alkylthio radicals, amino radicals, and amino radicals mono- di- or tri-substituted with a radical or radicals, which may be identical or different, chosen from ($C_1$–$C_6$)alkyl, ($C_1$–$C_6$)alkylcarbonyl, amido and ($C_1$–$C_6$)alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylcarbonyl($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1, when x=0, then the linking arm D is attached to the nitrogen atom bearing the radicals $R_4$, $R_5$, and $R_6$, when x=1, then two of the radicals chosen from $R_4$, $R_5$, and $R_6$ form, together with the nitrogen atom to which they are attached, a saturated ring chosen from 5-, 6- and 7-membered rings and the linking arm D is linked to a carbon atom of the saturated ring; and Y is a counter-ion;

formula (III):

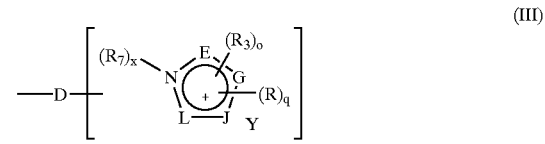

(III)

wherein

D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;

the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings;

q is an integer ranging from 0 to 4;

o is an integer ranging from 0 to 3;

q+o is an integer ranging from 0 to 4;

R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$) alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$) alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$) alkylsilane($C_1$–$C_6$)alkyl radicals, ($C_1$–$C_6$)alkoxy ($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals;

aryl radicals; benzyl radicals; $C_1$–$C_6$ aminoalkyl radicals; $C_1$–$C_6$ aminoalkyl radicals wherein the amine is substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarboxy($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
when x=0, the linking arm D is attached to the nitrogen atom,
when x=1, the linking arm D is attached to one of the ring members chosen from E, G, J and L, and Y is a counter-ion;

formula (IV):

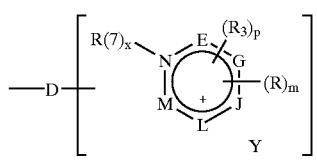

(IV)

wherein:

D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;

the ring members E, G, J, L and M, which may be identical or different, are each chosen from carbon, oxygen, sulphur and nitrogen atoms and form, together with the ring nitrogen, a ring chosen from pyridine, pyrimidine, pyrazine, triazine and pyridazine rings;

p is an integer ranging from 0 to 3;
m is an integer ranging from 0 to 5;
p+m is an integer ranging from 0 to 5;
R is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
when x=0, the linking arm D is attached to the nitrogen atom,
when x=1, the linking arm D is attached to one of the ring members chosen from E, G, J, L and M, and Y is a counter-ion.

24. The composition according to claim 23, further comprising at least one coupler chosen from meta-phenylenediamines, meta-aminophenols, meta-diphenols, naphthalenic couplers and heterocyclic couplers, and the addition salts thereof.

25. The composition according to claim 23, further comprising at least one additional oxidation base, other than the at least one oxidation base chosen from pyrrolidinyl-substituted para-phenylenediamine derivatives of formula (I) and the addition salts thereof, chosen from para-phenylenediamines, bis(phenyl)alkylenediamines, para-aminophenols, ortho-aminophenols and heterocyclic bases, and the addition salts thereof.

26. The composition according to claim 23, wherein the amount of the at least one oxidation base ranges from 0.001% to 10% by weight, relative to the total weight of the dye composition.

27. The composition according to claim 25, wherein the amount of the at least one additional oxidation base ranges from 0.001% to 10% by weight, relative to the total weight of the composition.

28. The composition according to claim 24, wherein the amount of the at least one coupler ranges from 0.001% to 10% by weight, relative to the total weight of the dye composition.

29. The composition according to claim 23, further comprising at least one direct dye chosen from nitrobenzene, azo, and methine direct dyes.

30. A process for oxidation dyeing of keratin fibers, comprising applying to the keratin fibers at least one dye composition comprising, in a medium suitable for dyeing, at least one oxidation base chosen from pyrrolidinyl-substituted para-phenylenediamine derivatives of formula (I) and the addition salts thereof:

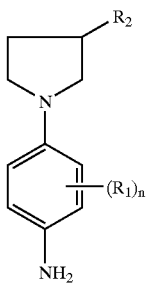

wherein:
n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains wherein at least one carbon atom may be replaced with an entity chosen from an oxygen atom, a nitrogen atom, a silicon atom, a sulphur atom, and a $SO_2$ radical, with the proviso that the radical $R_1$ does not comprise a peroxide bond, a diazo radical, a nitro radical or a nitroso radical, $R_2$ is chosen from onium radicals Z and radicals —X—C=$NR_8$—$NR_9R_{10}$, wherein
the X is chosen from oxygen and —$NR_{11}$ radicals; $R_8$, $R_9$, $R_{10}$ and $R_{11}$, which may be identical or different, are each chosen from hydrogen, $C_1$–$C_4$ alkyl radicals and $C_1$–$C_4$ hydroxyalkyl radicals;
the onium radicals Z are chosen from radicals of formulae (II), (III), and (IV):

formula (II):

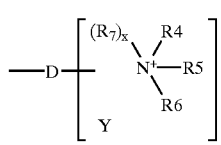

wherein
D is a linking arm chosen from a covalent bond and linear and branched $C_1$–$C_{14}$ alkylene chains which may be interrupted with at least one hetero atom chosen from oxygen, sulphur and nitrogen, and which may be substituted with at least one radical chosen from hydroxyl, $C_1$–$C_6$ alkoxy and amino radicals, and which may bear at least one ketone functional group;

$R_4$, $R_5$ and $R_6$, which may be identical or different, taken separately, are each chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$) alkylcarbonyl, amido and ($C_1$–$C_6$)alkylsulphonyl radicals; with the proviso that when the linking arm D is a covalent bond then $R_4$ is chosen from aryl radicals; benzyl radicals; $C_1$–$C_6$ amidoalkyl radicals; tri($C_1$–$C_6$) alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals;

Two of the radicals chosen from $R_4$, $R_5$ and $R_6$ form, together with the nitrogen atom to which they are attached, a saturated carbon-based cationic ring chosen from 4-, 5-, 6- and 7-membered rings optionally comprising at least one hetero atom, wherein the cationic ring may be substituted with at least one entity chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, ($C_1$–$C_6$)alkylcarbonyl radicals, thio radicals, $C_1$–$C_6$ thioalkyl radicals, ($C_1$–$C_6$)alkylthio radicals, amino radicals, and amino radicals mono- di- or tri-substituted with a radical or radicals, which may be identical or different, chosen from ($C_1$–$C_6$)alkyl, ($C_1$–$C_6$)alkylcarbonyl, amido and ($C_1$–$C_6$)alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylcarbonyl($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1,
when x=0, then the linking arm D is attached to the nitrogen atom bearing the radicals $R_4$, $R_5$, and $R_6$,
when x=1, then two of the radicals chosen from $R_4$, $R_5$, and $R_6$ form, together with the nitrogen atom to which they are attached, a saturated ring chosen from 5-, 6- and 7-membered rings and the linking arm D is linked to a carbon atom of the saturated ring; and Y is a counter-ion;

formula (III):

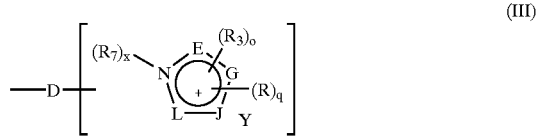

wherein
D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;

the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings;

q is an integer ranging from 0 to 4;

o is an integer ranging from 0 to 3;

q+o is an integer ranging from 0 to 4;

R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarboxy($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
when x=0, the linking arm D is attached to the nitrogen atom,
when x=1, the linking arm D is attached to one of the ring members chosen from E, G, J and L, and Y is a counter-ion;

formula (IV):

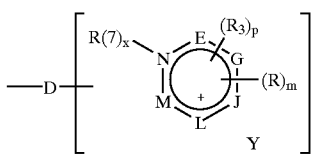

(IV)

wherein:
D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;

the ring members E, G, J, L and M, which may be identical or different, are each chosen from carbon, oxygen, sulphur and nitrogen atoms and form, together with the ring nitrogen, a ring chosen from pyridine, pyrimidine, pyrazine, triazine and pyridazine rings;

p is an integer ranging from 0 to 3;

m is an integer ranging from 0 to 5;

p+m is an integer ranging from 0 to 5;

R is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
when x=0, the linking arm D is attached to the nitrogen atom,
when x=1, the linking arm D is attached to one of the ring members chosen from E, G, J, L and M, and Y is a counter-ion;

and developing color using at least one oxidizing agent.

31. The process according to claim 30, wherein the at least one oxidizing agent is chosen from hydrogen peroxide, urea peroxide, alkali metal bromates, persalts, peracids and oxidase enzymes.

32. The process according to claim 31, wherein the at least one oxidizing agent is hydrogen peroxide.

33. The process according to claim 30, comprising mixing, at the time of use, the at least one oxidizing agent with the at least one dye composition.

34. The process according to claim 30, comprising applying to the keratin fibers at least one oxidizing composition comprising, in a medium suitable for dyeing, the at least one oxidizing agent, simultaneously with or sequentially to the at least one dye composition, in a medium suitable for dyeing.

35. A multi-compartment kit or device, comprising
a first compartment comprising a dye composition comprising, in a medium suitable for dyeing, at least one oxidation base chosen from pyrrolidinyl-substituted para-phenylenediamine derivatives of formula (I) and the addition salts thereof:

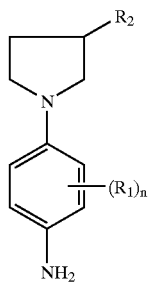

(I)

wherein:
n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains wherein at least one carbon atom may be replaced with an entity chosen from an oxygen atom, a nitrogen atom, a silicon atom, a sulphur atom, and a $SO_2$ radical, with the proviso that the radical $R_1$ does not comprise a peroxide bond, a diazo radical, a nitro radical or a nitroso radical, $R_2$ is chosen from onium radicals Z and radicals —X—C=$NR_8$—$NR_9R_{10}$, wherein
the X is chosen from oxygen and —$NR_{11}$ radicals; $R_8$, $R_9$, $R_{10}$ and $R_{11}$, which may be identical or different, are each chosen from hydrogen, $C_1$–$C_4$ alkyl radicals and $C_1$–$C_4$ hydroxyalkyl radicals;
the onium radicals Z are chosen from radicals of formulae (II), (III), and (IV):
formula (II):

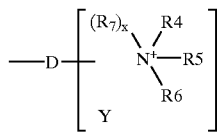

(II)

wherein
D is a linking arm chosen from a covalent bond and linear and branched $C_1$–$C_{14}$ alkylene chains which may be interrupted with at least one hetero atom chosen from oxygen, sulphur and nitrogen, and which may be substituted with at least one radical chosen from hydroxyl, $C_1$–$C_6$ alkoxy and amino radicals, and which may bear at least one ketone functional group;
$R_4$, $R_5$ and $R_6$, which may be identical or different, taken separately, are each chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals; with the proviso that when the linking arm D is a covalent bond then $R_4$ is chosen from aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals, Two of the radicals chosen from $R_4$, $R_5$ and $R_6$ form, together with the nitrogen atom to which they are attached, a saturated carbon-based cationic ring chosen from 4-, 5-, 6- and 7-membered rings optionally comprising at least one hetero atom, wherein the cationic ring may be substituted with at least one entity chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_{1-6}$)alkylsilane($C_1$–$C_6$)alkyl radicals, amido radicals, carboxyl radicals, ($C_1$–$C_6$)alkylcarbonyl radicals, thio radicals, $C_1$–$C_6$ thioalkyl radicals, ($C_1$–$C_6$)alkylthio radicals, amino radicals, and amino radicals mono- di- or tri-substituted with a radical or radicals, which may be identical or different, chosen from ($C_1$–$C_6$)alkyl, ($C_1$–$C_6$)alkylcarbonyl, amido and ($C_1$–$C_6$)alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1,
when x=0, then the linking arm D is attached to the nitrogen atom bearing the radicals $R_4$, $R_5$, and $R_6$,
when x=1, then two of the radicals chosen from $R_4$, $R_5$, and $R_6$ form, together with the nitrogen atom to which they are attached, a saturated ring chosen from 5-, 6- and 7-membered rings and the linking arm D is linked to a carbon atom of the saturated ring; and
Y is a counter-ion;
formula (III):

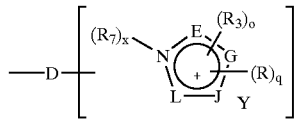

(III)

wherein
D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;
the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings,
q is an integer ranging from 0 to 4;
o is an integer ranging from 0 to 3;
q+o is an integer ranging from 0 to 4;
R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom,
$R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom,
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarboxy($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
when x=0, the linking arm D is attached to the nitrogen atom,
when x=1, the linking arm D is attached to one of the ring members chosen from E, G, J and L, and
Y is a counter-ion;
formula (IV):

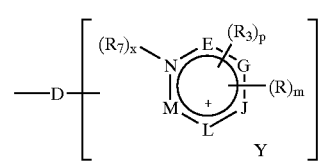

(IV)

wherein:
D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;
the ring members E, G, J, L and M, which may be identical or different, are each chosen from carbon, oxygen, sulphur and nitrogen atoms and form, together with the ring nitrogen, a ring chosen from pyridine, pyrimidine, pyrazine, triazine and pyridazine rings;
p is an integer ranging from 0 to 3;
m is an integer ranging from 0 to 5;
p+m is an integer ranging from 0 to 5;
R is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom,
$R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom,
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals, N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
   when x=0, the linking arm D is attached to the nitrogen atom,
   when x=1, the linking arm D is attached to one of the ring members chosen from E, G, J, L and M, and Y is a counter-ion;

and a second compartment comprising at least one oxidizing agent.

36. A process for the dyeing of keratin fibers, comprising applying to the keratin fibers a dyeing composition comprising, in a medium suitable for dyeing, at least one oxidation base chosen from pyrrolidinyl-substituted para-phenylenediamine derivatives of formula (I) and the addition salts thereof:

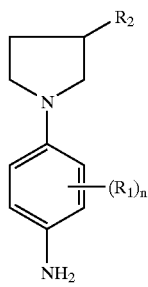
(I)

wherein:

n ranges from 0 to 4, wherein when n is greater than or equal to 2, then the radicals $R_1$ may be identical or different, $R_1$ is chosen from halogens; onium radicals Z; and $C_1$–$C_6$ aliphatic and alicyclic, saturated and unsaturated hydrocarbon-based chains wherein at least one carbon atom may be replaced with an entity chosen from an oxygen atom, a nitrogen atom, a silicon atom, a sulphur atom, and a $SO_2$ radical, with the proviso that the radical $R_1$ does not comprise a peroxide bond, a diazo radical, a nitro radical or a nitroso radical, $R_2$ is chosen from onium radicals Z and radicals —X—C=$NR_8$—$NR_9R_{10}$, wherein
   the X is chosen from oxygen and —$NR_{11}$ radicals; $R_8$, $R_9$, $R_{10}$ and $R_{11}$, which may be identical or different, are each chosen from hydrogen, $C_1$–$C_4$ alkyl radicals and $C_1$–$C_4$ hydroxyalkyl radicals;
   the onium radicals Z are chosen from radicals of formulae (II), (III), and (IV):
formula (II):

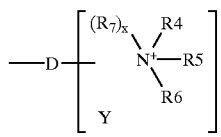
(II)

wherein

D is a linking arm chosen from a covalent bond and linear and branched $C_1$–$C_{14}$ alkylene chains which may be interrupted with at least one hetero atom chosen from oxygen, sulphur and nitrogen, and which may be substituted with at least one radical chosen from hydroxyl, $C_1$–$C_6$ alkoxy and amino radicals, and which may bear at least one ketone functional group;

$R_4$, $R_5$ and $R_6$, which may be identical or different, taken separately, are each chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$)alkoxy($C_1$–$C_6$)alkyl radicals; aryl radicals; benzyl radicals; $C_1$–$C_6$ amidoalkyl radicals; tri($C_1$–$C_6$)alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$) alkylcarbonyl, amido and ($C_1$–$C_6$)alkylsulphonyl radicals; with the proviso that when the linking arm D is a covalent bond then $R_4$ is chosen from aryl radicals; benzyl radicals; $C_1$–$C_6$ amidoalkyl radicals; tri($C_1$–$C_6$) alkylsilane($C_1$–$C_6$)alkyl radicals; $C_1$–$C_6$ aminoalkyl radicals; and $C_1$–$C_6$ aminoalkyl radicals wherein the amine is mono- or disubstituted with a radical or two radicals, which may be identical or different, chosen from $C_1$–$C_4$ alkyl, ($C_1$–$C_6$)alkylcarbonyl, amido and ($C_1$–$C_6$)alkylsulphonyl radicals, two of the radicals chosen from $R_4$, $R_5$ and $R_6$ form, together with the nitrogen atom to which they are attached, a saturated carbon-based cationic ring chosen from 4-, 5-, 6- and 7-membered rings optionally comprising at least one hetero atom, wherein the cationic ring may be substituted with at least one entity chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri ($C_1$–$C_6$)alkylsilane($C_1$–$C_6$)alkyl radicals, amido radicals, carboxyl radicals, ($C_1$–$C_6$)alkylcarbonyl radicals, thio radicals, $C_1$–$C_6$ thioalkyl radicals, ($C_1$–$C_6$)alkylthio radicals, amino radicals, and amino radicals mono- di- or tri-substituted with a radical or radicals, which may be identical or different, chosen from ($C_1$–$C_6$)alkyl, ($C_1$–$C_6$)alkylcarbonyl, amido and ($C_1$–$C_6$)alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylcarbonyl($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1,
   when x=0, then the linking arm D is attached to the nitrogen atom bearing the radicals $R_4$, $R_5$, and $R_6$,
   when x=1, then two of the radicals chosen from $R_4$, $R_5$, and $R_6$ form, together with the nitrogen atom to which they are attached, a saturated ring chosen from 5-, 6- and 7-membered rings and the linking arm D is linked to a carbon atom of the saturated ring; and Y is a counter-ion;

formula (III):

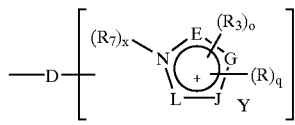

wherein

D is a linking arm chosen from a covalent bond and linear and branched $C_1$–$C_{14}$ alkylene chains that may be interrupted with at least one hetero atom chosen from oxygen, sulphur and nitrogen, and that may be substituted with at least one radical chosen from hydroxyl, $C_1$–$C_6$ alkoxy and amino radicals, and that may bear at least one ketone functional group;

the ring members E, G, J and L, which may be identical or different, are each chosen from carbon, oxygen, sulphur and nitrogen atoms to form, together with the ring nitrogen, a ring chosen from pyrrole, pyrazole, imidazole, triazole, oxazole, isoxazole, thiazole and isothiazole rings, q is an integer ranging from 0 to 4;

o is an integer ranging from 0 to 3;

q+o is an integer ranging from 0 to 4;

R, which may be identical or different, is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy ($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylcarboxy($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

x is 0 or 1 when x=0, the linking arm D is attached to the nitrogen atom, when x=1, the linking arm D is attached to one of the ring members chosen from E, G, J and L, and Y is a counter-ion;

formula (IV):

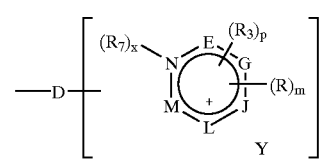

wherein:

D is a linking arm chosen from a covalent bond and linear and branched $C_1$–$C_{14}$ alkylene chains which may be interrupted with at least one hetero atom chosen from oxygen, sulphur and nitrogen atoms, and which may be substituted with at least one hydroxyl, $C_1$–$C_6$ alkoxy and amino radicals, and which may bear at least one ketone functional group;

the ring members E, G, J, L and M, which may be identical or different, are each chosen from carbon, oxygen, sulphur and nitrogen atoms and form, together with the ring nitrogen, a ring chosen from pyridine, pyrimidine, pyrazine, triazine and pyridazine rings;

p is an integer ranging from 0 to 3;

m is an integer ranging from 0 to 5;

p+m is an integer ranging from 0 to 5;

R is chosen from halogens, a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, amido radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with at least one radical chosen from ($C_1$–$C_6$)alkyl, ($C_1$–$C_6$)alkylcarbonyl, amido and ($C_1$–$C_6$)alkylsulphonyl radicals; $C_1$–$C_6$ monohydroxyalkyl radicals and $C_2$–$C_6$ polyhydroxyalkyl radicals; it being understood that the radical R is borne by a carbon atom, $R_3$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$) alkoxy($C_1$–$C_6$)alkyl radicals, $C_1$–$C_6$ carbamylalkyl radicals, ($C_1$–$C_6$)alkylcarboxy($C_1$–$C_6$)alkyl radicals and benzyl radicals; it being understood that the radical $R_3$ is borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical or two radicals, which may be identical or different, chosen from ($C_1$–$C_6$)alkyl, ($C_1$–$C_6$)alkylcarbonyl, amido and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N-($C_1$–$C_6$)alkylcarbamyl($C_1$–$C_6$)alkyl radicals; and N-($C_1$–$C_6$)alkylsulphonamido($C_1$–$C_6$)alkyl radicals;

x is 0 or 1
  when x=0, the linking arm D is attached to the nitrogen atom,
  when x=1, the linking arm D is attached to one of the ring members chosen from E, G, J, L and M, and Y is a counter-ion.

\* \* \* \* \*

UNITED STATES PATENT AND TRADEMARK OFFICE
CERTIFICATE OF CORRECTION

PATENT NO. : 6,946,005 B2
DATED : September 20, 2005
INVENTOR(S) : Sabelle et al.

It is certified that error appears in the above-identified patent and that said Letters Patent is hereby corrected as shown below:

Column 51,
Lines 17-22, in the structure for formula (III),

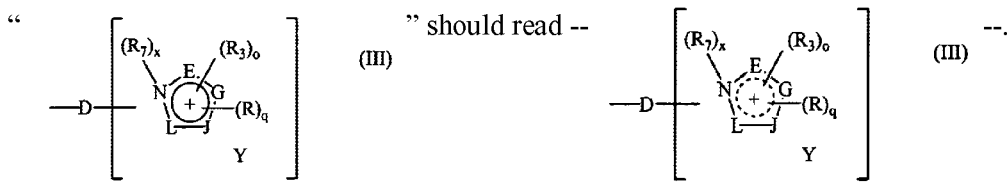

Column 52,
Line 4, "$C_1$-C6 carbamylalkyl" should read -- $C_1$-$C_6$ carbamylalkyl --.
Lines 21-27, in the structure for formula (IV),

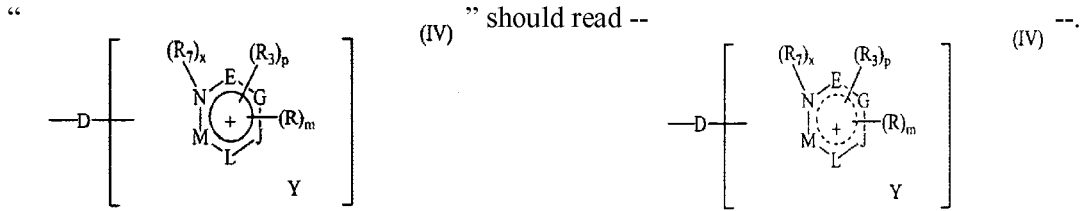

Column 53,
Line 42, "formula (II):" should read -- formula (II), --.
Lines 49-50, "tri($C_1$-$C_6$)alkyl" should read -- tri($C_1$-$C_6$)-alkylsilane($C_1$-$C_6$)alkyl --.
Line 52, "are, attached," should read -- are attached, --.
Line 67, "formula (II):" should read -- formula (II), --.

Column 54,
Lines 27-28, "N-($C_1$-$C_6$)alkylcarbamyl($C_1$-$C_6$)alkly" should read
-- N-($C_1$-$C_6$)alkylcarbamyl($C_1$-$C_6$)alkyl --.
Line 31, "alkylene, chain" should read -- alkylene chain --.

Column 56,
Lines 26-27, "[1-(4-Amino-3-methylphenyl)-pyrrolidine-3yl]-oxophosphorylcholine."
should read -- [1-(4-Amino-3-methylphenyl)-pyrrolidine-3-yl]-
oxophosphorylcholine. --.

UNITED STATES PATENT AND TRADEMARK OFFICE
CERTIFICATE OF CORRECTION

PATENT NO.     : 6,946,005 B2
DATED          : September 20, 2005
INVENTOR(S)    : Sabelle et al.

It is certified that error appears in the above-identified patent and that said Letters Patent is hereby corrected as shown below:

Column 58,
Lines 19-24, in structure for fomula (III),
" 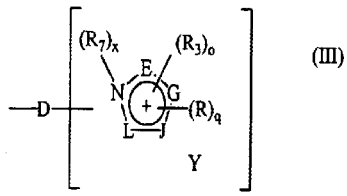 " should read -- 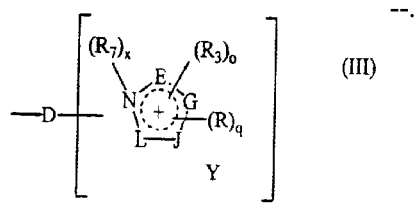 --.

Column 59,
Lines 24-30, in the structure for formula (IV),
" 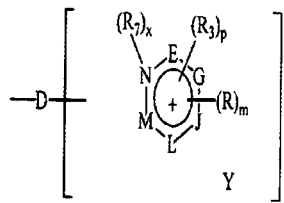 " should read -- 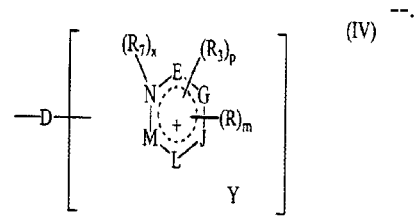 --.

Column 62,
Lines 51-56, in the structure for formula (III),
" 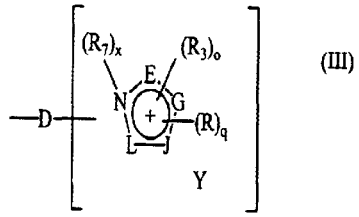 " should read -- 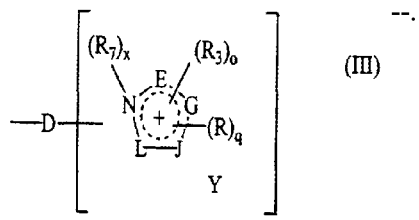 --.

UNITED STATES PATENT AND TRADEMARK OFFICE
CERTIFICATE OF CORRECTION

PATENT NO. : 6,946,005 B2
DATED : September 20, 2005
INVENTOR(S) : Sabelle et al.

It is certified that error appears in the above-identified patent and that said Letters Patent is hereby corrected as shown below:

Column 63,
Lines 55-61, in the structure for formula (IV),
" 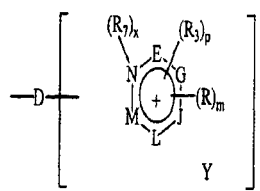 " should read -- 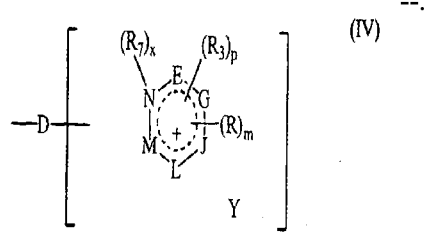 --.

Column 66,
Lines 31-32, "tri($C_{1-6}$)alkylsilane($C_1$-$C_6$)alkyl" should read
-- tri($C_1$-$C_6$)alkylsilane($C_1$-$C_6$)alkyl --.

Column 67,
Lines 6-11, in the structure for formula (III),
" 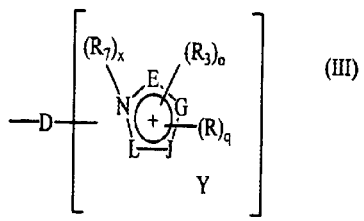 " should read -- 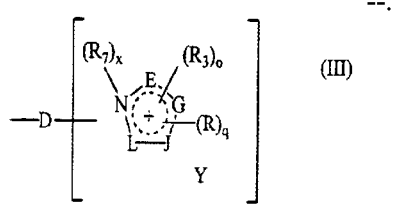 --.

Column 68,
Lines 9-15, in the structure for formula (IV),
" 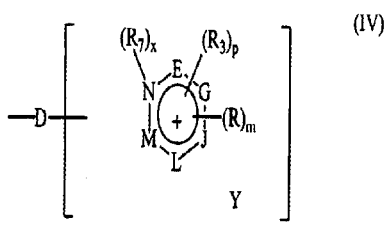 " should read -- 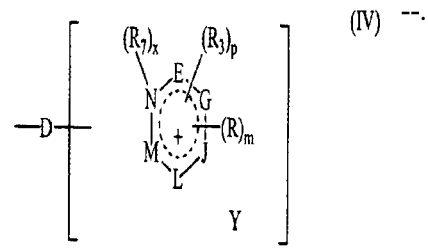 --.

UNITED STATES PATENT AND TRADEMARK OFFICE
CERTIFICATE OF CORRECTION

PATENT NO.   : 6,946,005 B2
DATED        : September 20, 2005
INVENTOR(S)  : Sabelle et al.

It is certified that error appears in the above-identified patent and that said Letters Patent is hereby corrected as shown below:

Column 70,
Line 26, "two" should read -- Two --.

Column 71,
Lines 6-11, in the structure for formula (III),
" " should read --

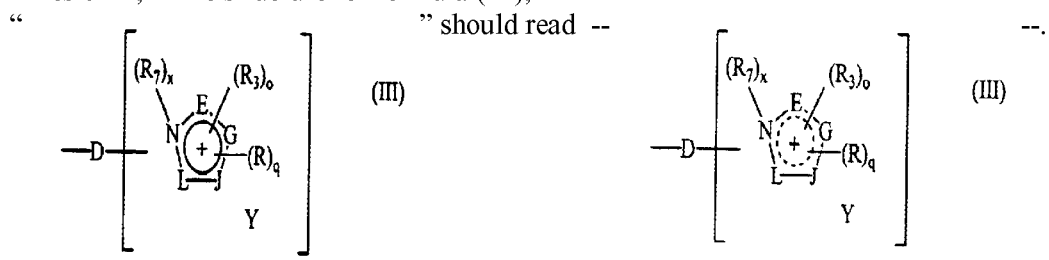

Column 72,
Lines 16-22, in the structure for formula (IV),
" " should read --

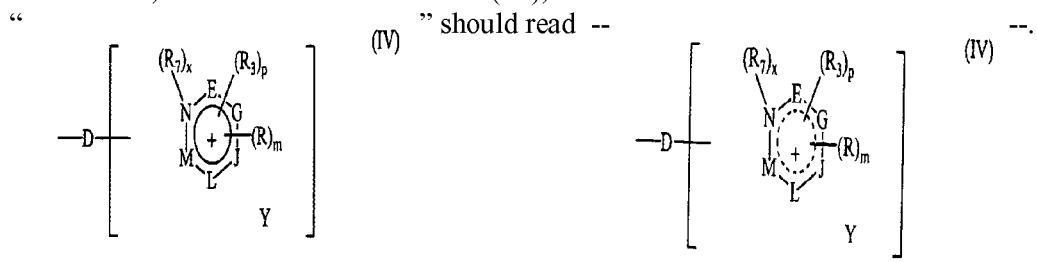

Signed and Sealed this

Sixth Day of June, 2006

JON W. DUDAS
*Director of the United States Patent and Trademark Office*